United States Patent
Ye

(10) Patent No.: US 11,796,618 B2
(45) Date of Patent: Oct. 24, 2023

(54) SYSTEMS AND METHODS FOR MAGNETIC RESONANCE IMAGING

(71) Applicant: SHANGHAI UNITED IMAGING HEALTHCARE CO., LTD., Shanghai (CN)

(72) Inventor: Yongquan Ye, Houston, TX (US)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 1025 days.

(21) Appl. No.: 16/510,285

(22) Filed: Jul. 12, 2019

(65) Prior Publication Data
US 2021/0011104 A1 Jan. 14, 2021

(51) Int. Cl.
G01R 33/563 (2006.01)
A61B 5/055 (2006.01)
G01R 33/56 (2006.01)
G16H 30/40 (2018.01)
G01R 33/561 (2006.01)

(52) U.S. Cl.
CPC ............ *G01R 33/563* (2013.01); *A61B 5/055* (2013.01); *G01R 33/5608* (2013.01); *G01R 33/5611* (2013.01); *G16H 30/40* (2018.01)

(58) Field of Classification Search
CPC .............. G01R 33/563; G01R 33/5608; G01R 33/5611; A61B 5/055; G16H 30/40
See application file for complete search history.

(56) References Cited

U.S. PATENT DOCUMENTS

| 5,998,996 A * | 12/1999 | Bernstein ......... G01R 33/56581 324/309 |
| 6,388,441 B1 | 5/2002 | Chen |
| 2004/0032259 A1 | 2/2004 | Dixon et al. |

(Continued)

FOREIGN PATENT DOCUMENTS

| CN | 106597337 A | 4/2017 |
| CN | 108294753 A | 7/2018 |

OTHER PUBLICATIONS

J.B.M. Warntjes et al., Rapid Magnetic Resonance Quantification on the Brain: Optimization for Clinical Usage, Magnetic Resonance in Medicine, 60: 320-329, 2008.

(Continued)

*Primary Examiner* — Christopher Koharski
*Assistant Examiner* — Sean A Frith
(74) *Attorney, Agent, or Firm* — METIS IP LLC

(57) ABSTRACT

A system is provided in the present disclosure. The system may acquire a first set of echo signals and a second set of echo signals relating to a subject. The first and the second set may be generated by using an MR scanner to execute a first acquisition and a second acquisition on the subject, respectively. The first acquisition may include at least a first repetition and a second repetition with different repetition times. Each of the first and second repetitions may have a first flip angle. The second acquisition may include at least a third repetition and a fourth repetition with different repetition times. Each of the third repetition and the fourth repetition may have a second flip angle different from the first flip angle. The system may also perform a measurement on the subject based on at least one of the first set or the second set.

20 Claims, 41 Drawing Sheets

(56) References Cited

U.S. PATENT DOCUMENTS

| | | | |
|---|---|---|---|
| 2010/0086184 A1 | 4/2010 | Kruger et al. | |
| 2010/0142774 A1* | 6/2010 | Ben-Haim | G16H 70/60 |
| | | | 382/128 |
| 2011/0105884 A1 | 5/2011 | Beck | |
| 2014/0070804 A1* | 3/2014 | Huang | G01R 33/34 |
| | | | 324/309 |
| 2016/0131729 A1* | 5/2016 | Kang | G01R 33/50 |
| | | | 324/309 |
| 2016/0313430 A1* | 10/2016 | Nickel | A61B 5/055 |
| 2018/0017652 A1 | 1/2018 | Ye | |
| 2018/0031653 A1 | 2/2018 | Boernert et al. | |
| 2018/0081004 A1 | 3/2018 | Yang | |
| 2018/0092569 A1* | 4/2018 | Li | A61B 5/055 |
| 2018/0143272 A1 | 5/2018 | Liu | |
| 2018/0231628 A1* | 8/2018 | Kuang | G01R 33/56536 |
| 2018/0231631 A1 | 8/2018 | Ye et al. | |
| 2018/0275235 A1 | 9/2018 | Reeder et al. | |
| 2018/0292503 A1 | 10/2018 | Slavin et al. | |
| 2018/0338701 A1 | 11/2018 | Amemiya et al. | |
| 2019/0053735 A1* | 2/2019 | Hu | A61B 5/055 |
| 2019/0064295 A1 | 2/2019 | Wang et al. | |
| 2019/0094324 A1 | 3/2019 | Seo et al. | |
| 2019/0250231 A1* | 8/2019 | Taniguchi | G01R 33/5618 |
| 2019/0318511 A1 | 10/2019 | Ye | |
| 2020/0090382 A1 | 3/2020 | Huang et al. | |
| 2020/0126231 A1 | 4/2020 | Hu et al. | |
| 2020/0300951 A1 | 9/2020 | Ye et al. | |

OTHER PUBLICATIONS

J.B.M. Warntjes et al., Novel Method for Rapid, Simultaneous T1, T2*, and Proton Density Quantification, Magnetic Resonance in Medicine, 57: 528-537, 2007.

Wang Yu et al., STrategically Acquired Gradient Echo (STAGE) imaging, part II: Correcting for RF inhomogeneities in estimating T1 and proton density, Magnetic Resonance Imaging, 46: 140-150, 2018.

Chen Yongsheng et al., STrategically Acquired Gradient Echo (STAGE) imaging, part I: Creating enhanced T1 contrast and standardized susceptibility weighted imaging and quantitative susceptibility mapping, Magnetic Resonance Imaging, 46: 130-139, 2018.

Ma Dan et al., Magnetic Resonance Fingerprinting, Nature, 495: 187-192, 2013.

Vasily L. Yarnykh, Actual Fiip-angle Imaging in the Pulsed Steady State: A Method for Rapid Three-dimensional Mapping of the Transmitted Radiofrequency Field, Magnetic Resonance in Medicine, 57: 192-200, 2007.

Kay Nehrke, On the Steady-state Properties of Actual Flip Angle Imaging (AFI), Magnetic Resonance in Medicine, 61: 84-92, 2009.

Sean C.L. Deoni, High-Resolution T1 Mapping of the Brain at 3T with Driven Equilibrium Single Pulse Observation of T1 with High-Speed Incorporation of RF Field Inhomogeneities (DESPOT1-HIFI), Journal of Magnetic Resonance Imaging, 26: 1106-1111, 2007.

Tokunori Kimura et al., Hybrid of Opposite-contrast MR Angiography (HOP-MRA) Combining Time-of-flight and Flow-Sensitive Black-Blood Contrasts, Magnetic Resonance in Medicine, 62: 450-458, 2009.

Ye Yongquan et al., Noncontrast-Enhanced Magnetic Resonance Angiography and Venography Imaging With Enhanced Angiography, Journal of Magnetic Resonance Imaging, 38: 1539-1548, 2013.

Gary H. Glover, Multipoint Dixon Technique for Water and Fat Proton and Susceptibility Imaging, Journal of Magnetic Resonance Imaging, 1(5): 521-530, 1991.

Scott B. Reeder et al., Homodyne Reconstruction and IDEAL Water-Fat Decomposition, Magnetic Resonance in Medicine, 54: 586-593, 2005.

Xiang Qing-San, Two-Point Water-Fat Imaging With Partially-Opposed-Phase (POP) Acquisition: An Asymmetric Dixon Method, Magnetic Resonance in Medicine, 56: 572-584, 2006.

Ajay Kumar Boyat et al., A Review Paper: Noise Models in Digital Image Processing, Signal & Image Processing: An International Journal, 6(2): 63-75, 2015.

Bidhult S. et al., Validation of a New T2* Algorithm and Its Uncertainty Value for Cardiac and Liver Iron Load Determination from MRI Magnitude Images, Magnetic Resonance in Medicine, 75: 1717-1729, 2016.

Hesper T. et al., T2* Mapping for Articular Cartilage Assessment: Principles, Current Applications, and Future Prospects, Skeletal Radiol, 43: 1429-1445, 2014.

Wu Bing et al., Fast and Tissue-Optimized Mapping of Magnetic Susceptibility and T2* with Multi-Echo and Multi-Shot Spirals, Neuroimage, 59(1): 297-305, 2012.

First Office Action in Chinese Application No. 202010327688.X dated Dec. 31, 2021, 22 pages.

* cited by examiner

SYSTEMS AND METHODS FOR MAGNETIC RESONANCE IMAGING

TECHNICAL FIELD

The present disclosure generally relates to magnetic resonance imaging (MRI), and more particularly, methods and systems for performing a measurement on a subject in MRI.

BACKGROUND

MRI systems are widely used in medical diagnosis and/or treatment by exploiting a powerful magnetic field and radio frequency (RF) techniques. During a medical diagnosis and/or treatment on a subject, various measurements, such as a longitudinal relaxation time (T1) measurement, a transverse relaxation time (T2) measurement, a proton density (PD) measurement, a B0 field measurement, etc., may need to be performed on the subject to provide a basis for the disease diagnosis and/or treatment. Conventionally, multiple MR pulse sequences may be applied on the subject to acquire different sets of MR data used in different measurements, which may be inefficient and cause unnecessary radiations on the subject. Therefore, it is desirable to provide effective systems and methods for collecting MR data suitable for various measurements and/or performing measurement(s) on the subject based on the collected MR data.

SUMMARY

According to one aspect of the present disclosure, a system is provided. The system may include at least one storage device including a set of instructions for MRI, and at least one processor configured to communicate with the at least one storage device. When executing the instructions, the at least one processor may be configured to direct the system to perform the following operations. The at least one processor may be configured to direct the system to acquire a first set of echo signals and a second set of echo signals relating to a subject. The first set may be generated by using an MR scanner to execute a first acquisition on the subject, and the second set may be generated by using the MR scanner to execute a second acquisition on the subject. The first acquisition may include at least a first repetition and a second repetition with different repetition times. Each of the first repetition and the second repetition may have a first flip angle. The second acquisition may include at least a third repetition and a fourth repetition with different repetition times. Each of the third repetition and the fourth repetition may have a second flip angle different from the first flip angle. The at least one processor may be also configured to direct the system to perform a measurement on the subject based on at least one of the first set or the second set.

In some embodiments, for each acquisition of the first acquisition and the second acquisition, during each of the repetitions in the acquisition, a plurality of echo signals may be acquired at a plurality of echo times.

In some embodiments, the measurement may relate to a fat-water separated image of the subject. To perform a measurement on the subject, the at least one processor may be further configured to direct the system to generate the fat-water separated image of the subject based on at least a portion of echo signals in at least one of the first set or the second set. The at least a portion of echo signals may correspond to at least one repetition in the first acquisition or the second acquisition.

In some embodiments, at least one repetition in the first acquisition or the second acquisition may include a flow modulation module.

In some embodiments, the measurement may relate to a magnetic resonance angiography (MRA) image. At least one repetition in the first acquisition or the second acquisition may include a first flow modulation module. At least one repetition in the first acquisition or the second acquisition may include a second flow modulation module different from the first flow modulation module. To perform a measurement on the subject, the at least one processor may be further configured to direct the system to generate at least one first image of the subject based on a first portion of echo signals in at least one of the first set or the second set. The first portion of echo signals may correspond to the at least one repetition having the first flow modulation module. The at least one processor may be further configured to direct the system to generate at least one second image of the subject based on a second portion of echo signals in at least one of the first set or the second set. The second portion of echo signals may correspond to the at least one repetition having the second flow modulation module. The at least one processor may be further configured to direct the system to generate the MRA image of the subject based on the at least one first image and the at least one second image.

In some embodiments, the measurement may relate to T1. To perform a measurement on the subject, the at least one processor may be further configured to direct the system to determine at least one of an actual flip angle or a B1 transmission field relating to the subject based on at least one of the first set or the second set. The at least one processor may be further configured to direct the system to perform the measurement relating to T1 on the subject based on the first set, the second set, and the at least one of the actual flip angle or the B1 transmission field relating to the subject.

In some embodiments, the measurement may relate to a virtual image of the subject. To perform a measurement on the subject, the at least one processor may be further configured to direct the system to generate one or more maps of the subject based on at least one of the first set or the second set, and generate the virtual image of the subject based on the one or more maps of the subject.

In some embodiments, the performing a measurement on the subject may be based on a multiple dimension integration (MDI) algorithm.

In some embodiments, the measurement may relate to a parameter of a physical point of the subject. To perform a measurement on the subject, the at least one processor may be further configured to direct the system to determine a signal representation of the physical point based on at least one of the first set or the second set. The signal representation may be associated with the parameter. The at least one processor may be further configured to direct the system to determine a value of the parameter of the physical point based on the signal representation of the physical point.

In some embodiments, to determine a signal representation of the physical point, the at least one processor may be further configured to direct the system to determine a plurality of signals of the physical point based on at least one of the first set or the second set. Each of the plurality of signals may correspond to a set of values in a plurality of signal dimensions of signal acquisition using the MR scanner. The at least one processor may be further configured to direct the system to determine a primary signal dimension and at least one secondary signal dimension among the plurality of signal dimensions. The primary signal dimension may be associated with the signal representation. The at least one processor may be further configured to direct the system to determine the primary signal dimension, and the at least one secondary signal dimension, the signal representation of the physical point based on the plurality of signals.

In some embodiments, the measurement may relate to at least one of a T1, a T2, a transverse relaxation decay (T2*), a signal decay rate (R2), a transverse relaxation rate (R2*), a B0 field, a B1 field, an actual flip angle, a PD, a water fraction, a fat fraction, a virtual image, an MR angiography image, a susceptibility weighted image (SWI), a T1 weighted image, a PD weighted image, an accentuated T1 weighted image, a T2 weighted image, a T2* weighted image, or a quantitative susceptibility map.

According to another aspect of the present disclosure, a method implemented on a computing device having at least one processor and at least one storage device for MRI is provided. The method may include acquiring a first set of echo signals and a second set of echo signals relating to a subject. The first set may be generated by using an MR scanner to execute a first acquisition on the subject, and the second set may be generated by using the MR scanner to execute a second acquisition on the subject. The first acquisition may include at least a first repetition and a second repetition with different repetition times. Each of the first repetition and the second repetition may have a first flip angle. The second acquisition may include at least a third repetition and a fourth repetition with different repetition times. Each of the third repetition and the fourth repetition may have a second flip angle different from the first flip angle. The method may also include performing a measurement on the subject based on at least one of the first set or the second set.

According to still another aspect of the present disclosure, non-transitory computer-readable storage medium including instructions for MRI is provided. When accessed by at least one processor of a system, the instructions causes the system to perform a method. The method may include acquiring a first set of echo signals and a second set of echo signals relating to a subject. The first set may be generated by using an MR scanner to execute a first acquisition on the subject, and the second set may be generated by using the MR scanner to execute a second acquisition on the subject. The first acquisition may include at least a first repetition and a second repetition with different repetition times. Each of the first repetition and the second repetition may have a first flip angle. The second acquisition may include at least a third repetition and a fourth repetition with different repetition times. Each of the third repetition and the fourth repetition may have a second flip angle different from the first flip angle. The method may also include performing a measurement on the subject based on at least one of the first set or the second set.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
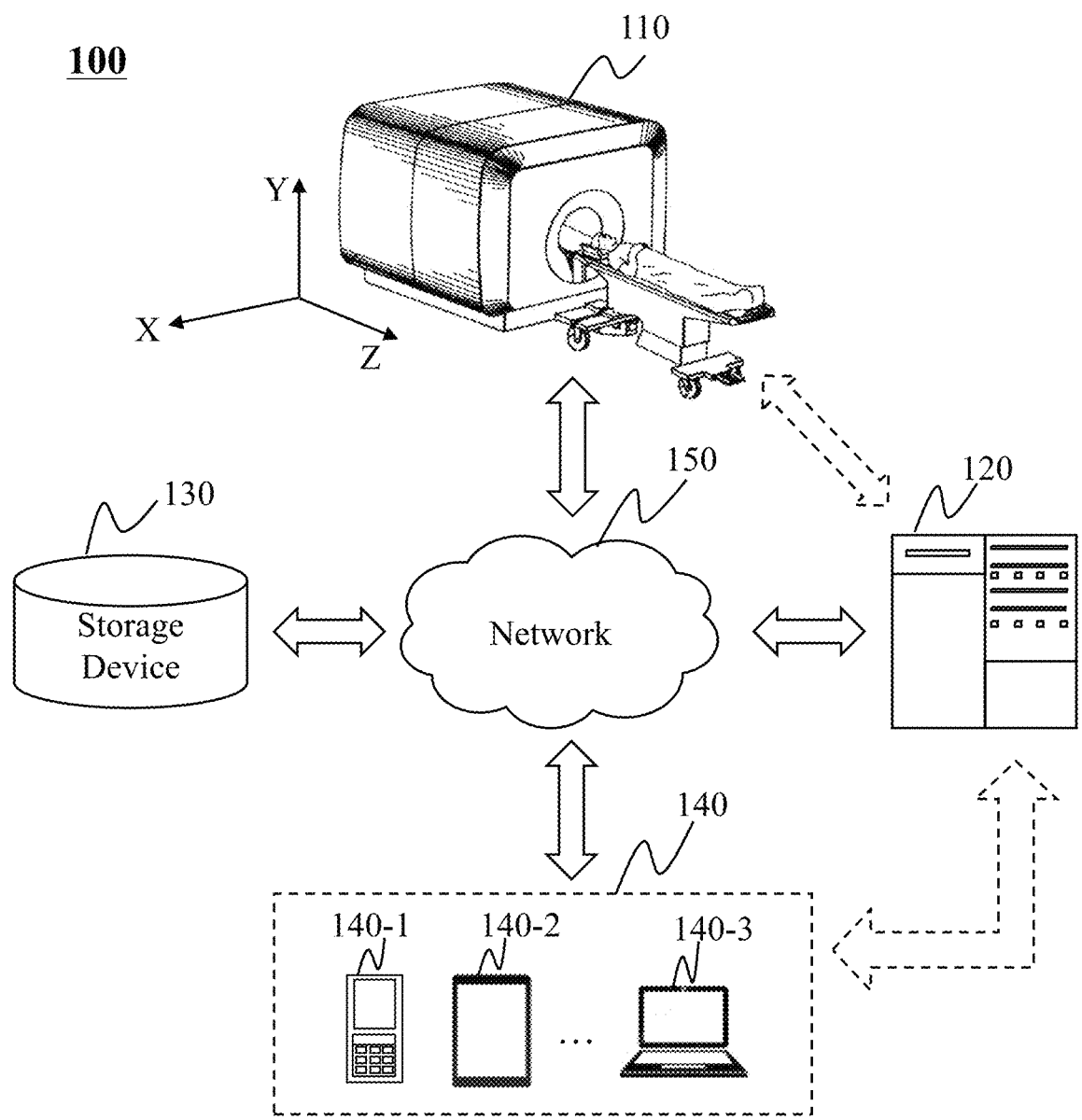
FIG. 1 is a schematic diagram illustrating an exemplary MRI system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "device," "unit," "module," and/or "block" used herein are one method to distinguish different components, elements, parts, section or assembly of different level in ascending order. However, the terms may be displaced by another expression if they achieve the same purpose.

As used herein, the term "and/or" includes any and all combinations of one or more of the associated listed items. The term "pixel" and "voxel" in the present disclosure are used interchangeably to refer to an element in an image. The term "image" in the present disclosure is used to refer to images of various forms, including a 2-dimensional image, a 3-dimensional image, a 4-dimensional image, etc.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood the operations of the flowcharts may be implemented not in order. Conversely, the operations may be implemented in inverted order, or simultaneously. Moreover, one or more other operations may be added to the flowcharts. One or more operations may be removed from the flowcharts.

Moreover, while the systems and methods disclosed in the present disclosure are described primarily regarding performing a measurement on a subject (e.g., a patient, a physical point of the patient) in an MRI system. It should be understood that this is only for illustration purposes. The systems and methods of the present disclosure may be applied to any other kind of medical imaging system. In some embodiments, the imaging system may include a single modality imaging system and/or a multi-modality imaging system. The single modality imaging system may include, for example, the MRI system. The multi-modality imaging system may include, for example, a computed tomography-magnetic resonance imaging (MRI-CT) system, a positron emission tomography-magnetic resonance imaging (PET-MRI) system, a single photon emission computed tomography-magnetic resonance imaging (SPECT-MRI) system, a digital subtraction angiography-magnetic resonance imaging (DSA-MRI) system, etc.

An aspect of the present disclosure relates to systems and methods for performing a measurement on a subject. The systems and methods may acquire a first set of echo signals and a second set of echo signals relating to a subject. The first set may be generated by using an MR scanner to execute a first acquisition on the subject, and the second set may be generated by using the MR scanner to execute a second acquisition on the subject. The first acquisition may include at least a first repetition and a second repetition with different repetition times. Each of the first repetition and the second repetition may have a first flip angle. The second acquisition may include at least a third repetition and a fourth repetition with different repetition times. Each of the third repetition and the fourth repetition may have a second flip angle different from the first flip angle. The systems and methods may also perform a measurement on the subject based on at least one of the first set or the second set.

According to some embodiments of the present disclosure, during at least one the first, second, third, and fourth repetitions, a plurality of echo signals at a plurality of echo times may be acquired. Optionally, at least one of the first, second, third, and fourth repetitions may include an FM module. In this way, more data relating to the subject, including data corresponding to different TEs, data corresponding to different flip angles, data corresponding to FM module(s), data corresponding to different TRs, may be acquired during the scan of the subject, which may improve an acquisition efficiency without lengthening the scan time. This may allow different measurements of the subject to be performed simultaneously based on a single scan, reducing the number (or count) of scans of the subject to collect data for different measurements, thereby reducing the scan time.

FIG. 1 is a schematic diagram illustrating an exemplary MRI system 100 according to some embodiments of the present disclosure. As shown in FIG. 1, the MRI system 100 may include an MR scanner 110, a processing device 120, a storage device 130, one or more terminals 140, and a network 150. In some embodiments, the MR scanner 110, the processing device 120, the storage device 130, and/or the terminal(s) 140 may be connected to and/or communicate with each other via a wireless connection, a wired connection, or a combination thereof. The connections between the components in the MRI system 100 may be variable. For example, the MR scanner 110 may be connected to the processing device 120 through the network 150. As another example, the MR scanner 110 may be connected to the processing device 120 directly.

The MR scanner 110 may be configured to scan a subject (or a part of the subject) to acquire image data, such as echo signals (or MR signals) associated with the subject. For example, the MR scanner 110 may detect a plurality of echo signals by applying an MR pulse sequence on the subject. In some embodiments, the MR scanner 110 may include, for example, a magnetic body, a gradient coil, an RF coil, etc., as described in connection with FIG. 2. In some embodiments, the MR scanner 110 may be a permanent magnet MR scanner, a superconducting electromagnet MR scanner, or a resistive electromagnet MR scanner, etc., according to types of the magnetic body. In some embodiments, the MR scanner 110 may be a high-field MR scanner, a mid-field MR scanner, and a low-field MR scanner, etc., according to the intensity of the magnetic field.

The subject may be biological or non-biological. For example, the subject may include a patient, a man-made object, etc. As another example, the subject may include a specific portion, organ, tissue, and/or a physical point of the patient. For example, the subject may include head, brain, neck, body, shoulder, arm, thorax, cardiac, stomach, blood vessel, soft tissue, knee, feet, or the like, or a combination thereof.

For illustration purposes, a coordinate system including an X axis, a Y-axis, and a Z-axis is provided in FIG. 1. The X axis and the Z axis shown in FIG. 1 may be horizontal, and the Y-axis may be vertical. As illustrated, the positive X direction along the X axis may be from the right side to the left side of the MRI scanner 110 seen from the direction facing the front of the MRI scanner 110; the positive Y direction along the Y axis shown in FIG. 1 may be from the lower part to the upper part of the MRI scanner 110; the positive Z direction along the Z axis shown in FIG. 1 may refer to a direction in which the subject is moved out of the scanning channel (or referred to as the bore) of the MRI scanner 110. More description of the MRI scanner 110 may be found elsewhere in the present disclosure. See, e.g., FIG. 2 and the description thereof.

The processing device 120 may process data and/or information obtained from the MR scanner 110, the storage device 130, and/or the terminal(s) 140. For example, the processing device 120 may generate an MR image by processing image data (e.g., echo signals) collected by the MR scanner 110. As another example, the processing device 120 may perform a measurement on the subject based on the image data. In some embodiments, the processing device 120 may be a single server or a server group. The server group may be centralized or distributed. In some embodiments, the processing device 120 may be local or remote. For example, the processing device 120 may access information and/or data from the MR scanner 110, the storage device 130, and/or the terminal(s) 140 via the network 150. As another example, the processing device 120 may be directly connected to the MR scanner 110, the terminal(s) 140, and/or the storage device 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be implemented by a computing device 300 having one or more components as described in connection with FIG. 3.

The storage device 130 may store data, instructions, and/or any other information. In some embodiments, the storage device 130 may store data obtained from the MR scanner 110, the processing device 120, and/or the terminal(s) 140. In some embodiments, the storage device 130 may store data and/or instructions that the processing device 120 may execute or use to perform exemplary methods described in the present disclosure. In some embodiments, the storage device 130 may include a mass storage device, a removable storage device, a volatile read-and-write memory, a read-only memory (ROM), or the like, or a combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), a digital versatile disk ROM, etc. In some embodiments, the storage device 130 may be implemented on a cloud platform as described elsewhere in the disclosure.

In some embodiments, the storage device 130 may be connected to the network 150 to communicate with one or more other components in the MRI system 100 (e.g., the MR scanner 110, the processing device 120, and/or the terminal(s) 140). One or more components of the MRI system 100 may access the data or instructions stored in the storage device 130 via the network 150. In some embodiments, the storage device 130 may be part of the processing device 120 or the terminal(s) 140.

The terminal(s) 140 may be configured to enable a user interaction between a user and the MRI system 100. For example, the terminal(s) 140 may receive an instruction to cause the MR scanner 110 to scan the subject from the user. As another example, the terminal(s) 140 may receive a processing result (e.g., a measurement result, such as a value of a quantitative parameter or a quantitative map relating to the subject) from the processing device 120 and display the processing result to the user. In some embodiments, the terminal(s) 140 may be connected to and/or communicate with the MR scanner 110, the processing device 120, and/or the storage device 130. In some embodiments, the terminal(s) 140 may include a mobile device 140-1, a tablet computer 140-2, a laptop computer 140-3, or the like, or a combination thereof. For example, the mobile device 140-1 may include a mobile phone, a personal digital assistant (PDA), a gaming device, a navigation device, a point of sale (POS) device, a laptop, a tablet computer, a desktop, or the like, or a combination thereof. In some embodiments, the terminal(s) 140 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the processing device 120 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the terminal(s) 140 may be part of the processing device 120 or the MR scanner 110.

The network 150 may include any suitable network that can facilitate the exchange of information and/or data for the MRI system 100. In some embodiments, one or more components of the MRI system 100 (e.g., the MR scanner 110, the processing device 120, the storage device 130, the terminal(s) 140, etc.) may communicate information and/or data with one or more other components of the MRI system 100 via the network 150. For example, the processing device 120 may obtain image data (e.g., an echo signal) from the MR scanner 110 via the network 150. As another example, the processing device 120 may obtain user instructions from the terminal(s) 140 via the network 150. The network 150 may include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, or the like, or a combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or a combination thereof. In some embodiments, the network 150 may include one or more network access points. For example, the network 150 may include wired and/or wireless network access points such as base stations and/or internet exchange points through which one or more components of the MRI system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and characteristics of the exemplary embodiments described herein may be combined in various ways to obtain additional and/or alternative exemplary embodiments. In some embodiments, the MRI system 100 may include one or more additional components and/or one or more components described above may be omitted. Additionally or alternatively, two or more components of the MRI system 100 may be integrated into a single component. For example, the processing device 120 may be integrated into the MR scanner 110. As another example, a component of the MRI system 100 may be replaced by another component that can implement the functions of the component. In some embodiments, the storage device 130 may be a data storage including cloud computing platforms, such as a public cloud, a private cloud, a community and hybrid cloud, etc. However, those variations and modifications do not depart the scope of the present disclosure.

Figure 2:
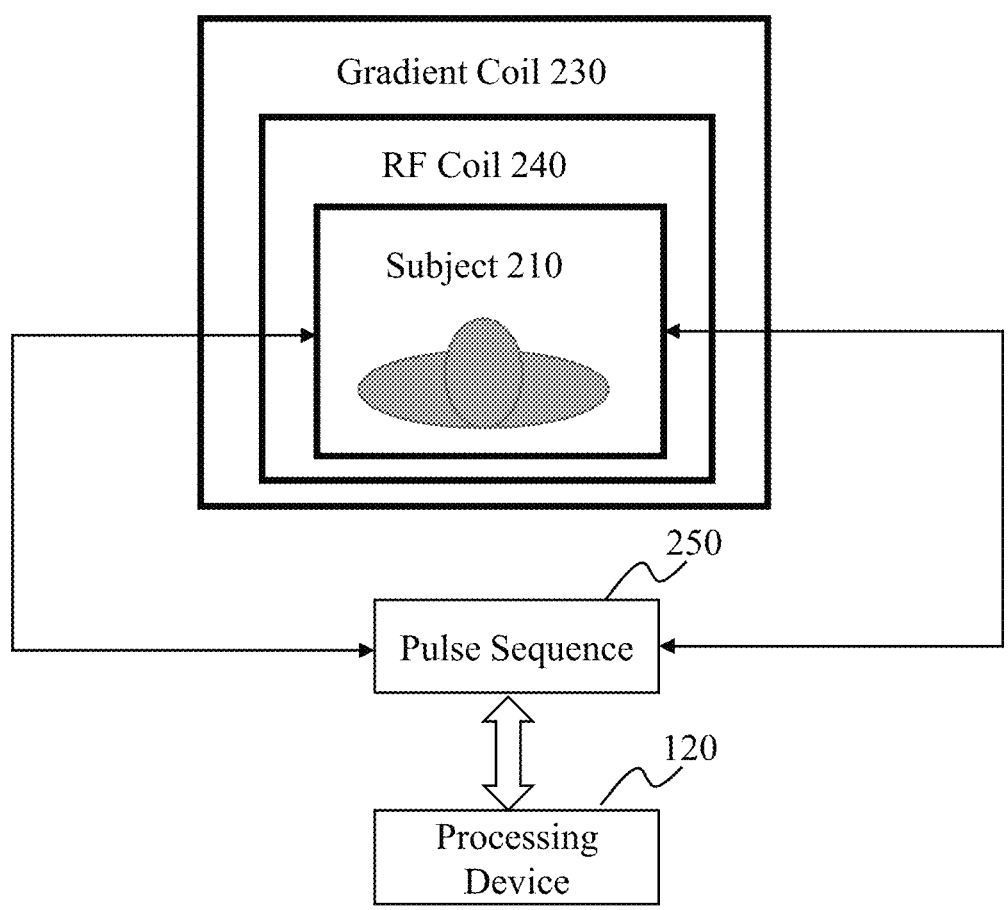
FIG. 2 is a block diagram illustrating an exemplary MR scanner according to some embodiments of the present disclosure.

FIG. 2 is a block diagram illustrating an exemplary MR scanner 110 according to some embodiments of the present disclosure. As illustrated in FIG. 2, the MR scanner 110 may include a magnetic body 220, a gradient coil 230, an RF coil 240, and a pulse sequence module 250.

The magnetic body 220 may generate a static magnetic field during the scanning of at least a portion of a subject 210. The magnetic body 220 may be of various types including, for example, a permanent magnet, a superconducting electromagnet, a resistive electromagnet, etc.

The gradient coil 230 may provide magnetic field gradients to the main magnetic field in an X direction, a Y direction, and/or a Z direction. As used herein, the X direction, the Y direction, and the Z direction may represent an X axis, a Y-axis, and a Z-axis in a coordinate system (e.g., a same or similar coordinate system as that described in FIG. 1). For example, the Z-axis may be along the axis of the magnetic body 220, the X-axis and the Z-axis may form a horizontal plane, and the X-axis and the Y-axis may form a vertical plane. In some embodiments, the gradient coil 230 may include an X-direction coil for providing a magnetic field gradient to the main magnetic field in the X direction, a Y-direction coil for providing a magnetic field gradient to the main magnetic field in the Y direction, and/or Z-direction coil for providing a magnetic field gradient to the main magnetic field in the Z direction. In some embodiments, the X-direction coil, the Y-direction coil, and/or the Z-direction coil may be of various shape or configuration. For example, the Z-direction coil may be designed based on a circular (Maxwell) coil. As another example, the X-direction coil and the Y-direction coil may be designed on the basis of a saddle (Golay) coil configuration.

The RF coil 240 may emit RF pulse signals to and/or receive echo signals from the subject 210 being examined. In some embodiments, the RF coil 240 may include a transmitting coil and a receiving coil. The transmitting coil may emit signals (e.g., RF pulses) that may excite a nucleus in the subject 210 to provide a resonation. The receiving coil may receive echo signals emitted from the subject 210. In some embodiments, the RF transmitting coil and the RF receiving coil may be integrated into one same coil. In some embodiments, the RF coil 240 may be of various types including, for example, a quadrature detection (QD) orthogonal coil, a phased-array coil, a specific element spectrum coil, etc. In some embodiments, the RF coil 240 may be a phased-array coil that includes multiple coil units, each of which may detect echo signals independently.

In some embodiments, the RF coil 240 may be used to detect signals generated by an MR pulse sequence. The MR pulse sequence may be of various types, such as a spin echo (SE) pulse sequence, a gradient refocused echo (GRE) pulse sequence, an inversion recovery (IR) pulse sequence, a multi-echo MR pulse sequence, a T1ρ-prepared pulse sequence, a T2-prepared pulse sequence, a diffusion-weighted imaging (DWI) pulse sequence, a saturation recovery (SR) pulse sequence, a steady-state pulse sequence, etc. As used herein, the multi-echo MR pulse sequence may refer to a pulse sequence in which a plurality of signals of a plurality of echoes are produced (or detected) after every excitation pulse. The T1ρ-prepared pulse sequence may refer to a pulse sequence that includes a T1ρ weighted magnetization preparation pulse (also referred to as a spin-lock pulse). The T2-prepared pulse sequence may refer to a pulse sequence that includes a T2 preparation pulse. The DWI pulse sequence may refer to a pulse sequence (normally a spin echo sequence) having a pair of diffusion-sensitizing gradients applied before and after, e.g., a 180-degree pulse in the pulse sequence. The SR pulse sequence may refer to a partial saturation pulse sequence in which a preceding pulse leaves the spins in a state of saturation, so that recovery at the time of a next pulse has taken place from an initial condition of no magnetization. The steady-state pulse sequence may refer to a pulse sequence in which a longitudinal magnetization and/or a transverse magnetization in each repetition are kept constant to reach an equilibrium or steady-state.

In some embodiments, the MR pulse sequence may be defined by one or more parameters including, for example, the type of the MR pulse sequence, a time for applying the MR pulse sequence, a duration of the MR pulse sequence, a flip angle of an excitation pulse in the MR pulse sequence, a count (or number) of RF pulses in the MR pulse sequence, a repetition time (TR), a repetition count, an inversion time (TI), a count (or number) of acquisitions in the MR pulse sequence, a b-value, a T1ρ-preparation duration, a T2-preparation duration, an echo train length, an echo spacing, a velocity encoding (VENC) value, etc. As used herein, an FA of an excitation pulse may refer to the rotation of the net magnetization vector by the excitation pulse relative to the main magnetic field. The TR may refer to the timespan between two repeating and consecutive RF pulses in an MR pulse sequence (e.g., the time span between two consecutive excitation RF pulses in an SE pulse sequence, the timespan between two consecutive 180° inversion pulses in an IR pulse sequence). The repetition count may refer to the count (or number) of repetitions in an MR pulse sequence. The TI may refer to the timespan between a 180° inversion pulse and a following 90° excitation pulse in an IR pulse sequence. The b-value may refer to a factor that reflects the strength and timing of diffusion-sensitizing gradients in a DWI pulse sequence. The T1ρ-preparation duration may refer to the duration of a spin-lock pulse in a T1ρ-prepared pulse sequence. The T2-preparation duration may refer to the duration of a T2 preparation pulse in a T2-prepared pulse sequence.

In some embodiments, the RF coil 240 may detect (or receive) one or more echo signals corresponding to one or more echoes excited by the MR pulse sequence. In some embodiments, an echo signal (or an echo) may be defined by one or more parameters, for example, an echo signal type (a spin echo, a fast spin echo (FSE), a fast recovery FSE, a single shot FSE, a gradient recalled echo, a fast imaging with steady-state precession), an echo time (TE), an echo signal intensity, a coil unit (e.g., denoted by an identification (ID) or a serial number of the coil unit) that detects the echo signal, a repetition (e.g., denoted by a repetition serial number) in which the echo signal is detected, an acquisition (e.g., denoted by an acquisition serial number) in which the echo signal is detected, etc. The TE may refer to the time between an application of an excitation RF pulse and the peak of an echo excited by the excitation RF pulse.

The pulse sequence module 250 may be configured to define parameters and arrangements relating to the MR scanner 110 before and/or during the scan of the subject 210. In some embodiments, the parameters relating to the MR scanner 110 may include one or more parameters relating to an MR pulse sequence (e.g., the type of the MR pulse sequence, a TR, a repetition count, a TI, etc.) applied by the MR scanner 110, one or more parameters relating to a gradient field generated by the gradients coil 230 or a radiofrequency field (e.g. an RF center frequency, a flip angle), one or more parameters relating to echo signals (e.g., a TE, a spin echo type) detected by the RF coil 240 as described elsewhere in the disclosure, or the like, or any combination thereof. In some embodiments, the parameters relating to the MR scanner 110 may include one or more other imaging parameters, such as, a count (or number) of RF channels, an image contrast and/or ratio, a slice thickness, an imaging type (e.g., a T1 weighted imaging, a T2 weighted imaging, a proton density weighted imaging, etc.), a field of view (FOV) of the MR scanner 110, an off-center frequency shift of the MR scanner 110, or the like, or a combination thereof.

In some embodiments, the pulse sequence module 250 may be connected to and/or communicate with the processing device 120. For example, before an MRI scanning process, at least one portion of the parameters and arrangements relating to the MR scanner 110 may be designed and/or determined by the processing device 120 according to clinical demands or a scanning protocol, and transmitted to the pulse sequence module 250. In an MR scanning process, the MR scanner 110 may scan the subject 210 based on the parameters and arrangements defined by the pulse sequence module 250. For example, the MR scanner 110 may apply an MR pulse sequence with specific parameters relating to MR pulse sequences defined by the pulse sequence module 250, and the RF coil 240 may receive echo signals according to specific parameters relating to echo signals defined by the pulse sequence module 250.

In some embodiments, an echo signal and data generated based on the echo signal (e.g., image data or K-space data) may be defined by the parameters relating to the MR scanner 110 under which the echo signal is acquired using the MR scanner 110. For example, the parameters relating to the MR scanner 110 under which the echo signal is acquired may be regarded as a plurality of signal dimension of the echo signal and the data generated based on the echo signal. In some embodiments, an image of the subject 210 may be generated based on the echo signal. The image data of a specific physical point of the subject 210 in the image may be considered as a signal of the specific physical point. The signal of the specific physical point may have a plurality of signal dimensions. A signal dimension of the signal may refer to a parameter that describes an instance under which the signal is determined or acquired using the MRI scanner 110. The signal dimensions of the signal may include, for example, one or more parameters relating to the MRI scanner 110 during the scan of the subject 210, one or more parameters relating to the determination of the signal based on the corresponding image (e.g., a coordinate of a corresponding pixel in the image), etc. Exemplary parameters relating to the MR scanner 110 during the scan may include one or more parameters relating to the MR pulse sequence (e.g., a TE, a TR, a TI, a b-value, a T1ρ-preparation duration, a T2-preparation duration, a velocity encoding value, a repetition, an acquisition) applied during the scan, one or more parameters relating to a gradient field or radiofrequency field (e.g. an RF center frequency, a flip angle) applied during the scan, one or more other imaging parameters (e.g., a count (or number) of RF channels, a coil unit) of the MR scanner 110, or the like, or any combination thereof. More descriptions regarding the signal dimensions may be found elsewhere in the present disclosure. See, e.g., FIG. 6 and relevant descriptions thereof.

This description regarding the MR scanner 110 provided above is intended to be illustrative, and not to limit the scope of the present disclosure. Many alternatives, modifications, and variations will be apparent to those skilled in the art. The features, structures, methods, and characteristics of the exemplary embodiments described herein may be combined in various ways to obtain additional and/or alternative exemplary embodiments. For example, the pulse sequence module 250 may be integrated into the processing device 120. However, those variations and modifications do not depart the scope of the present disclosure.

Figure 3:
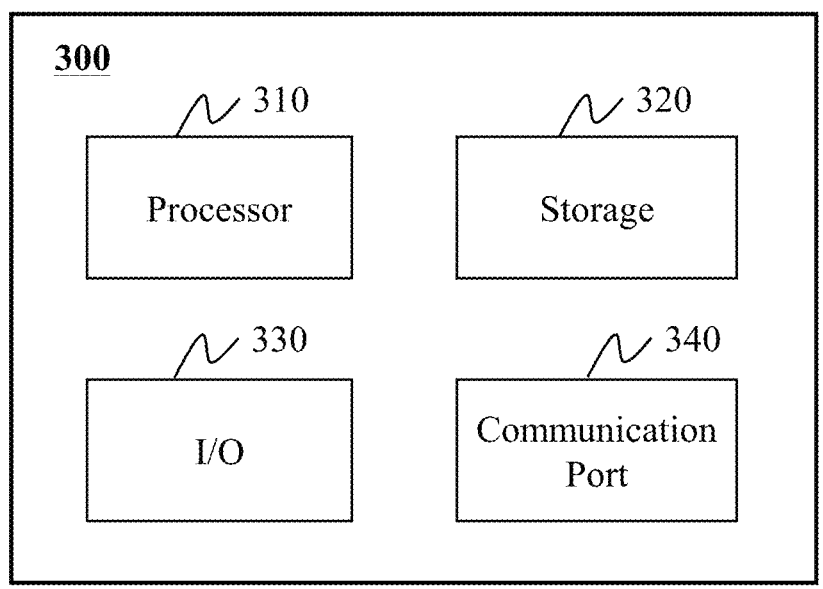
FIG. 3 is a schematic diagram illustrating exemplary hardware and/or software components of a computing device according to some embodiments of the present disclosure.

FIG. 3 is a schematic diagram illustrating exemplary hardware and/or software components of a computing device 300 according to some embodiments of the present disclosure. In some embodiments, one or more components of the MRI system 100 may be implemented on one or more components of the computing device 300. Merely by way of example, the processing device 120 and/or the terminal(s) 140 may be implemented one or more components of the computing device 300, respectively.

As illustrated in FIG. 3, the computing device 300 may include a processor 310, a storage 320, an input/output (I/O) 330, and a communication port 340. The processor 310 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 310 may process image data of a subject obtained from the MR scanner 110, the storage device 130, terminal(s) 140, and/or any other component of the MRI system 100. In some embodiments, the processor 310 may generate a quantitative map or an image of the subject based on image data of the subject acquired by the MR scanner 110.

In some embodiments, the processor 310 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or a combinations thereof.

Merely for illustration, only one processor is described in the computing device 300. However, it should be noted that the computing device 300 in the present disclosure may also include multiple processors. Thus operations and/or method steps that are performed by one processor as described in the present disclosure may also be jointly or separately performed by the multiple processors. For example, if in the present disclosure the processor of the computing device 300 executes both operation A and operation B, it should be understood that operation A and operation B may also be performed by two or more different processors jointly or separately in the computing device 300 (e.g., a first processor executes operation A and a second processor executes operation B, or the first and second processors jointly execute operations A and B).

The storage 320 may store data/information obtained from the MR scanner 110, the storage device 130, the terminal(s) 140, and/or any other component of the MRI system 100. In some embodiments, the storage 320 may include a mass storage device, a removable storage device, a volatile read-and-write memory, a read-only memory (ROM), or the like, or a combination thereof. For example, the mass storage device may include a magnetic disk, an optical disk, a solid-state drive, etc. The removable storage device may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 320 may store one or more programs and/or instructions to perform exemplary methods described in the present disclosure. For example, the storage 320 may store a program for the processing device 120 for determining a signal representation.

The I/O 330 may input and/or output signals, data, information, etc. In some embodiments, the I/O 330 may enable a user interaction with the computing device 300 (e.g., the processing device 120). In some embodiments, the I/O 330 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 340 may be connected to a network (e.g., the network 150) to facilitate data communications. The communication port 340 may establish connections between the computing device 300 (e.g., the processing device 120) and one or more components of the MRI system 100 (e.g., the MR scanner 110, the storage device 130, and/or the terminal(s) 140). The connection may be a wired connection, a wireless connection, any other communication connection that can enable data transmission and/or reception, and/or a combination of these connections. The wired connection may include, for example, an electrical cable, an optical cable, a telephone wire, or the like, or a combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 340 may be and/or include a standardized communication port, such as RS232, RS485, etc. In some embodiments, the communication port 340 may be a specially designed communication port. For example, the communication port 340 may be designed in accordance with the digital imaging and communications in medicine (DICOM) protocol.

Figure 4:
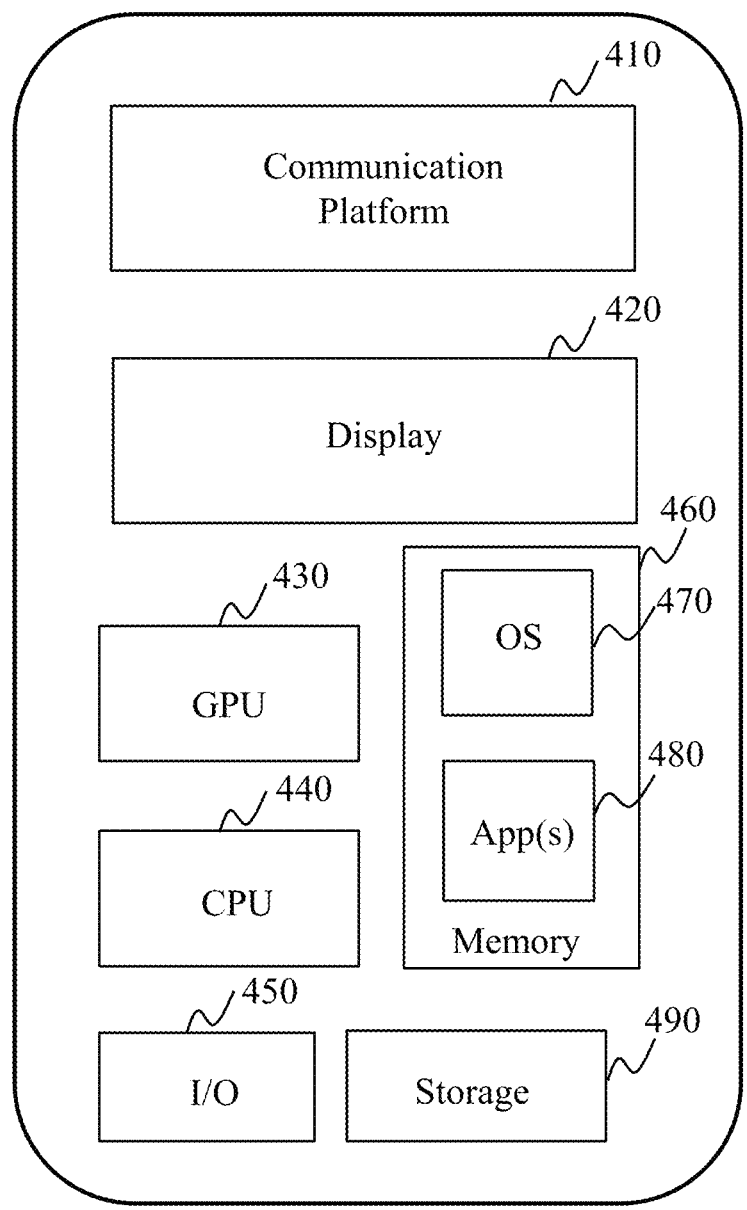
FIG. 4 is a schematic diagram illustrating exemplary hardware and/or software components of a mobile device according to some embodiments of the present disclosure.

FIG. 4 is a schematic diagram illustrating exemplary hardware and/or software components of a mobile device 400 may be implemented according to some embodiments of the present disclosure. In some embodiments, one or more components of the MRI system 100 may be implemented on one or more components of the mobile device 400. Merely by way of example, a terminal 140 may be implemented on one or more components of the mobile device 400.

As illustrated in FIG. 4, the mobile device 400 may include a communication platform 410, a display 420, a graphics processing unit (GPU) 430, a central processing unit (CPU) 440, an I/O 450, a memory 460, and a storage 490. In some embodiments, any other suitable component, including but not limited to a system bus or a controller (not shown), may also be included in the mobile device 400. In some embodiments, a mobile operating system 470 (e.g., iOS™, Android™, Windows Phone™, etc.) and one or more applications 480 may be loaded into the memory 460 from the storage 490 in order to be executed by the CPU 440. The applications 480 may include a browser or any other suitable mobile apps for receiving and rendering information relating to the MRI system 100. User interactions with the information stream may be achieved via the I/O 450 and provided to the processing device 120 and/or other components of the MRI system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 5:
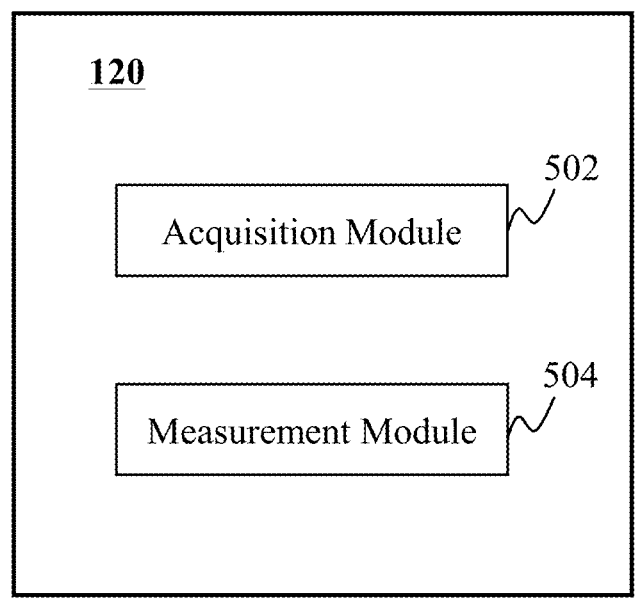
FIG. 5 is a block diagram illustrating an exemplary processing device according to some embodiments of the present disclosure.

FIG. 5 is a block diagram illustrating an exemplary processing device 120 according to some embodiments of the present disclosure. As shown in FIG. 5, the processing device 120 may include an acquisition module 502 and a measurement module 504.

Figure 7:
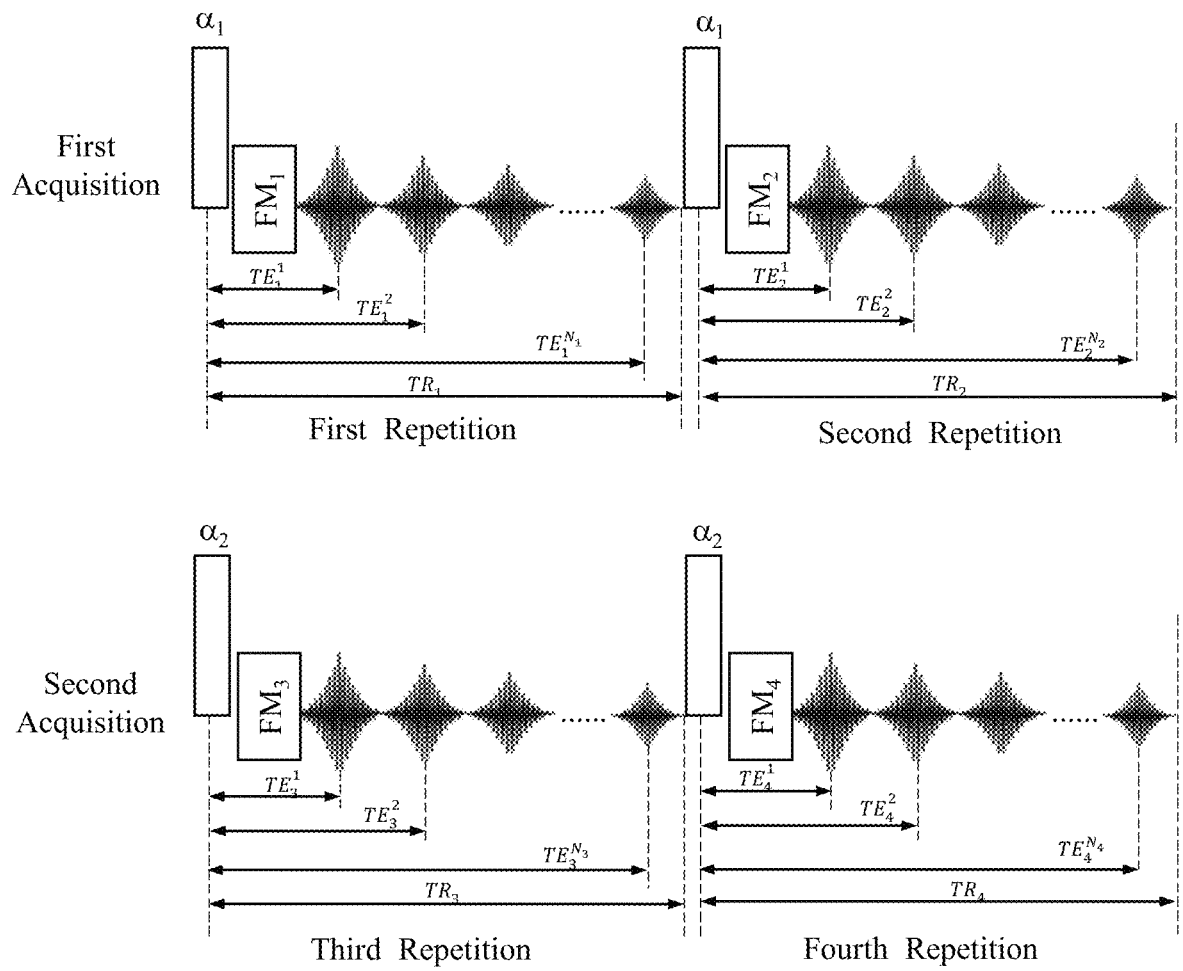
FIGS. 7 to 11 illustrate exemplary MR pulse sequences according to some embodiments of the present disclosure.

The acquisition module 502 may be configured to acquire information relating to the MRI system 100. For example, the acquisition module 502 may acquire scan data of a subject acquired by an MR scanner. The MR scanner may be directed to apply an MR pulse sequence on the subject and detect a plurality of echo signals excited by the MR pulse sequence. The acquisition module 502 may acquire the echo signals from the MR scanner and/or a storage device that stores the echo signals for further analysis. In some embodiments, the MR pulse sequence may include a same or similar configuration as an MR pulse sequence as illustrated in FIG. 7. For example, the MR pulse sequence may include a first acquisition and a second acquisition. The acquisition module 502 may acquire a first set of echo signals that is detected in the first acquisition and a second echo signals that is detected in the second acquisition. More descriptions regarding the MR pulse sequence, the first set, and the second set may be found elsewhere in the present disclosure. See, e.g., operation 601 and relevant descriptions thereof.

Generally, the word "module," "unit," or "block," as used herein in FIG. 5, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or themselves, and/or may be invoked in response to detected events or interrupts. Software modules/units/blocks configured for execution on computing devices (e.g., processor 310 as illustrated in FIG. 3) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may apply to a system, a device, or a portion thereof.

It will be understood that when a unit, device, module or block in FIG. 5 is referred to as being "on," "connected to," or "coupled to," another unit, device, module, or block, it may be directly on, connected or coupled to, or communicate with the other unit, device, module, or block, or an intervening unit, device, module, or block may be present, unless the context clearly indicates otherwise.

The measurement module 504 may be configured to perform a measurement on the subject based on scan data of the subject. The measurement performed on the subject may include determining a quantitative parameter of a physical point of the subject, generating a quantitative map of the subject (which includes a value of a quantitative parameter of each physical point of the subject), generating a specific image reflecting a physiological property of the subject, and/or any other measurement that can evaluate a characteristic of the subject. In some embodiments, the measurement may be performed based on a multiple dimension integration (MDI) algorithm. More descriptions regarding the measurement may be found elsewhere in the present disclosure. See, e.g., operation 602 and Examples 1-4 and relevant descriptions thereof.

In some embodiments, the modules may be hardware circuits of all or part of the processing device 120. The modules may also be implemented as an application or set of instructions read and executed by the processing device 120. Further, the modules may be any combination of the hardware circuits and the application/instructions. For example, the modules may be the part of the processing device 120 when the processing device 120 is executing the application/set of instructions.

It should be noted that the above description of the processing device 120 is provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. In some embodiments, the processing device 120 may further include one or more additional modules, such as a storage module. Additionally or alternatively, one or more of the modules described above may be omitted. In addition, any module mentioned above may be implemented in two or more separate units. For example, the measurement module 504 may be divided into a plurality of sub-units each of which is configured to perform one or more specific measurements on the subject.

Figure 6:
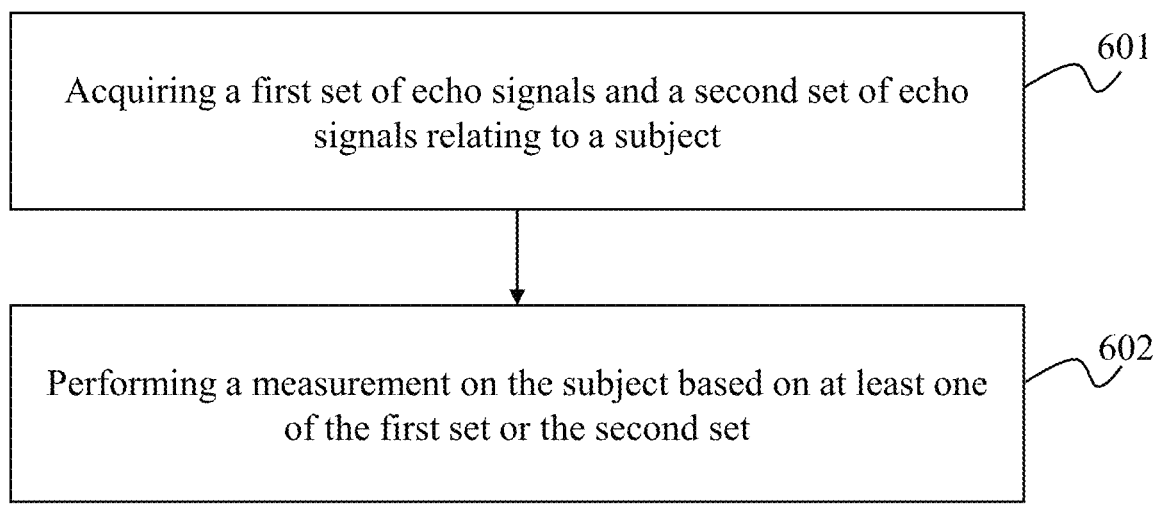
FIG. 6 is a flowchart illustrating an exemplary process for performing a measurement on a subject according to some embodiments of the present disclosure.

FIG. 6 is a flowchart illustrating an exemplary process for performing a measurement on a subject according to some embodiments of the present disclosure. In some embodiments, one or more operations of process 600 may be implemented in the MRI system 100 illustrated in FIG. 1. For example, the process 600 may be stored in a storage device (e.g., the storage device 130, the storage 320, and/or the storage 490) of the MRI system 100 in the form of instructions, and invoked and/or executed by the processing device 120 (e.g., the processor 310 of the computing device 300 as illustrated in FIG. 3, the CPU 440 of the mobile device 400 as illustrated in FIG. 4, one or more modules as illustrated in FIG. 5).

In 601, the processing device 120 (e.g., the acquisition module 502, the interface circuits of the processor 310) may acquire a first set of echo signals and a second set of echo signals relating to the subject. As used herein, the subject may refer to any biological or non-biological subject, such as a patient (or a portion of the patient), a man-made object (e.g., a phantom).

In some embodiments, the first and second sets of echo signals may be acquired by using an MR scanner (e.g., the MR scanner 110) to execute a scan on the subject. During the scan, the MR scanner may apply an MR pulse sequence on the subject. For illustration purposes, an exemplary MR pulse sequence 700 is provided in FIG. 7. As shown in FIG. 7, the MR pulse sequence 700 corresponds to a first acquisition and a second acquisition. The first set of echo signals may be excited in the first acquisition and the second set of echo signals may be excited in the second acquisition. Each of the first acquisition and the second acquisition may include a plurality of repetitions. For example, the first acquisition may include at least a first repetition and a second repetition. The second acquisition may include at least a third repetition and a fourth repetition. The first, second, third, and fourth repetitions may have a repetition time $TR_1$, a repetition time $TR_2$, a repetition time $TR_3$, and a repetition time $TR_4$, respectively.

The repetitions in a single acquisition may have a same repetition time or different repetition times, i.e., $TR_1$ may be equal to or different from $TR_2$, and $TR_3$ may be equal to or different from $TR_4$. The first and third repetitions may have a same repetition time or different repetition times, i.e., $TR_3$ may be equal to or different from $TR_1$. The second and fourth repetitions may have a same repetition time or different repetition times, i.e., $TR_4$ may be equal to or different from $TR_2$.

Each repetition in an acquisition of the MR pulse sequence 700 may include an excitation pulse having a certain flip angle. In some embodiments, the flip angles of different repetitions in the same acquisition may be the same or different. For example, as shown in FIG. 7, the excitation pulses in the first and second repetitions of the first acquisition both have a flip angle $\alpha_1$. The excitation pulses in the third and fourth repetitions of the second acquisition both have a flip angle $\alpha_2$. The flip angle $\alpha_2$ may be equal to or different from the flip angle $\alpha_1$. In some embodiments, the flip angle $\alpha_2$ may be different from the flip angle $\alpha_1$, such that data sets with different flip angles may be acquired. In some embodiments, the process 600 may be implemented to perform a T1 measurement on the subject. The accuracy of T1 measurement may be impacted by a B1 inhomogeneity (i.e., an inhomogeneous spatial distribution of B1 field). The B1 inhomogeneity may result in a discrepancy between an actual flip angle and the preset flip angle (e.g., $\alpha_1$ or $\alpha_2$) at a physical point of the subject. The data sets with different repetition times may be used to determine an actual flip angle at the physical point or an actual flip angle distribution in the subject, thus improving the accuracy of T1 measurement. More descriptions regarding the T1 measurement may be found elsewhere in the present disclosure. See, e.g., Example 1 and relevant descriptions thereof.

In some embodiments, during at least one repetition of the first acquisition and the second acquisition, a plurality of echo signals may be produced (or detected) at a plurality of echo times. For example, during each of the first, second, third, and fourth repetitions, a plurality of echo signals may be acquired at a plurality of echo times. As shown in FIG. 7, $N_1$ echo signals are sequentially detected in the first repetition of the first acquisition at echo times $TE_1^1$, $TE_1^2 \ldots$, and $TE_1^{N_1}$. $N_2$ echo signals are sequentially detected in the second repetition of the first acquisition at echo times $TE_2^1$, $TE_2^2, \ldots$, and $TE_2^{N_2}$. $N_1$ may be equal to or different from $N_2$. For example, $N_1$ may be equal to or smaller than $N_2$. The echo time of an $i^{th}$ (i being a positive integer equal to or smaller than $N_1$) echo signal in the first repetition may be same as the echo time of an $i^{th}$ echo signal in the prior $N_1$ echo signals in the second repetition, i.e., $TE_1^1=TE_2^1$, $TE_1^2=TE_2^2, \ldots$, and $TE_1^{N_1}=TE_2^{N_1}$. As another example, $N_1$ may be smaller than $N_2$, and the echo time of the $i^{th}$ echo signal in the first repetition may be different from the echo time of the $i^{th}$ echo signal in the prior $N_1$ echo signals in the second repetition, i.e., $TE_1^1 \neq TE_2^1$, $TE_1^2 \neq TE_2^2 \ldots$, and $TE_1^{N_1} \neq TE_2^{N_1}$.

Similarly, $N_3$ echo signals are sequentially detected in the third repetition of the second acquisition at echo times $TE_3^1$, $TE_3^2 \ldots$, and $TE_3^{N_3}$. $N_4$ echo signals are sequentially detected in the fourth repetition in the second acquisition at echo times $TE_4^1$, $TE_4^2, \ldots$, and $TE_4^4$. $N_3$ may be equal to or different from $N_4$. The echo time of an $j^{th}$ (j being a positive integer being equal to or smaller than $N_3$ and $N_4$) echo signal in the third repetition may be same as or different from the echo time of an $j^{th}$ echo signal in the fourth repetition.

Each of $N_1$, $N_2$, $N_3$, and $N_4$ may be a positive integer greater than 0. The sum of $N_1$ and $N_2$ may be equal to or different from the sum of $N_3$ and $N_4$. $N_1$ of the first repetition may be equal to or different from $N_3$ of the third repetition. For example, $N_1$ may be smaller than or equal to $N_3$. The echo time of an $i^{th}$ echo signal in the first repetition may be same as or different from the echo time of an $i^{th}$ echo signal in the prior $N_1$ echo signals in the third repetition. Similarly, $N_2$ of the second repetition may be equal to or different from $N_4$ of the fourth repetition. For example, $N_2$ may be smaller than or equal to $N_4$. The echo time of an $j^{th}$ echo signal in the second repetition may be same as or different from the echo time of an $j^{th}$ echo signal in the prior $N_2$ echo signals in the fourth repetition.

In some embodiments, at least one repetition in the first acquisition and the second acquisition may include a flow modulation (FM) module. Exemplary FM modules may include a flow compensation (FC) module, a flow dephasing (FD) module, a flow encoding (FE) module, or the like. An FM module may have an impact on a body fluid (e.g., blood) but have no or little impact on non-fluid tissue (e.g., a bone) in an MR scan. For example, the signal intensity of a body fluid at a certain echo time in a repetition during which an FC module is applied may be higher than that in a repetition during which an FD module is applied. As another example, the body fluid in a repetition during which a positive FE module is applied may have a positive phase, and the body fluid in a repetition during which a negative FE module is applied may have a negative phase.

As shown in FIG. 7, each repetition in the MR pulse sequence 700 may include an FM module. The FM modules in the first, second, third, and fourth repetitions are represented as $FM_1$, $FM_2$, $FM_3$, and $FM_4$, respectively. $FM_1$, $FM_2$, $FM_3$, and $FM_4$ may be of a same type or different types. For example, the $FM_1$, $FM_2$, $FM_3$, and $FM_4$ may all be an FC module. In some embodiments, at least two of the $FM_1$, $FM_2$, $FM_3$, and $FM_4$ may be of different types. For example, $FM_1$ and $FM_2$ in the first acquisition may be of a certain type (e.g., an FC module), and $FM_3$ and $FM_4$ may be of another type (e.g., an FD module). As another example, $FM_1$ and $FM_3$ may be of a certain type (e.g., a positive FE module), and $FM_2$ and $FM_4$ may be of another type (e.g., a negative FM module). In some embodiments, an MR pulse sequence incorporating one or more FM modules may be used to acquire image(s) in which a body fluid exhibits a specific characteristic, providing a basis for magnetic resonance angiography (MRA) imaging. More descriptions regarding MRA imaging may be found elsewhere in the present disclosure. See, e.g., Example 2 and relevant descriptions thereof.

In some embodiments, one or more other parameters of the MR pulse sequence 700, such as a VENC value, a parameter relating to a gradient field, etc., may have a constant value during the execution of the first and second acquisitions. Optionally, one or more imaging techniques, such as but not limited to a K-space acquisition technique, a parallel imaging technique, a compressed sensing technique, a K-space data sharing technique, etc., may be utilized during the execution of the MR pulse sequence 700 to accelerate the scanning progress.

It should be noted that the MR pulse sequence 700 is merely provided for the purposes of illustration, and not intended to limit the scope of the present disclosure. In some embodiments, the MR pulse sequence 700 may have a configuration different from the exemplary one illustrated in FIG. 7. For example, the MR pulse sequence 700 may have more than two acquisitions, for example, 3, 4, or 5 acquisitions. As another example, one or more of $N_1$, $N_2$, $N_3$, and $N_4$ may be equal to 1, that is, only one echo signal may be acquired in one or more of the first, second, third, and fourth repetitions. As yet another example, an acquisition of the MR pulse sequence 700 may include only one repetition. Additionally or alternatively, the MR pulse sequence 700 may include one or more additional components, and/or one or more components (e.g., one or more of $FM_1$, $FM_2$, $FM_3$, and $FM_4$) of the MR pulse sequence 700 described above may be omitted.

In some embodiments, the configuration of the MR pulse sequence 700 may be designed according to actual needs, such as the measurement(s) to be performed on the subject. For example, if a T1 measurement is to be performed, the flip angle $\alpha_2$ may need to be different from the flip angle $\alpha_1$. In some embodiments, the flip angle $\alpha_2$ may be different from the flip angle $\alpha_1$. A plurality of echo signals may be detected in each repetition in each acquisition. $TR_2$ of the second repetition may be different from $TR_1$ of the first repetition, and/or $TR_4$ of the fourth repetition may be different from $TR_3$ of the third repetition. At least two of the $FM_1$, $FM_2$, $FM_3$, and $FM_4$ may be of different types of FM modules. In this way, more data relating to the subject, including data corresponding to different TEs, data corresponding to different flip angles, data corresponding to different FM modules, data corresponding to different TRs, may be acquired during the scan of the subject, which improves an acquisition efficiency without lengthening the scan time. This enables that different measurements of the subject may be performed simultaneously based on a single scan, avoiding unnecessary and repeated scans on the subject.

In some embodiments, the MR scanner may include a plurality of coil units, each of which may be configured to detect echo signals independently during the scan of the subject. The first set and second set of echo signals may include echo signals detected by one of the coil units. For example, the first set may include echo signals detected by a certain coil unit in the first acquisition, and the second set may include echo signals detected by the certain coil unit in the second acquisition. Alternatively, the first set and second set of echo signals may include echo signals detected by two or more coil units. For example, the first set may include echo signals detected by each coil unit in the first acquisition, and the second set may include echo signals detected by each coil unit in the second acquisition.

In 602, the processing device 120 (e.g., the measurement module 504, the processing circuits of the processor 310) may perform a measurement on the subject based on at least one of the first set or the second set.

As used herein, a process (e.g., a measurement) "based on at least one of the first set or the second set" may refer to a process based on the first set (or a portion of the first set) and/or the second set (or a portion of the second set). A measurement performed on the subject may include determining a quantitative parameter of a physical point of the subject, generating a quantitative map of the subject (which includes a value of a quantitative parameter of each physical point of the subject), generating a specific image reflecting a physiological property of the subject, and/or any other measurement that can evaluate a characteristic of the subject. Exemplary quantitative parameters of a physical point may include a T1, a T2, a transverse relaxation decay (T2*), a signal decay rate (R2), a transverse relaxation rate (R2*), a B0 field, a B1 field, an actual flip angle, a proton density (PD), a water fraction, a fat fraction, or the like, or any combination thereof. Exemplary quantitative maps of the subject may include a T1 map, a T2 map, a T2* map, an R2 map, an R2* map, a B0 field distribution map, a B1 field distribution map, a PD distribution map, a water fraction distribution map, a fat fraction distribution map, a quantitative susceptibility (QS) map, or the like, or any combination thereof. Exemplary images of the subject may include a virtual image, an MRA image, a susceptibility weighted image (SWI), a T1 weighted image, a PD weighted image, an accentuated T1 weighted image, a T2 weighted image, a T2* weighted image, a fat-water separated image, or the like, or any combination thereof.

In some embodiments, the measurement result of the subject may include at least one of a basic image, a preliminary image, or an advanced image of the subject. As used herein, a basic image may refer to an image that is reconstructed directly based on one or more echo signals of the first set and/or the second set. A preliminary image may refer to an image that is generated based on one or more basic images. An advanced image may refer to an image that is generated based on one or more basic images and one or more preliminary images.

Exemplary basic images may include a T1 weighted image, a PD weighted image, a T2 weighted image, a T2* weighted image, a phase image, a bright blood image, a black blood image, a phase contrast MRA image, or the like, or any combination thereof. In some embodiments, a bright blood image may be generated based on an MR pulse sequence incorporating an FC module. A black blood image may be generated based on an MR pulse sequence incorporating an FD module. A phase contrast MRA image may be generated based on an MR pulse sequence incorporating an FE module (e.g., a positive FE module or a negative FE module). Exemplary preliminary images may include a T1 map, a T2 map, a T2* map, an R2 map, an R2* map, a B0 field distribution map, a B1 field distribution map, a PD distribution map, a fat-water separated image (e.g., a water-only image, a fat-only image), a water fraction distribution map, a fat fraction distribution map, a QS map, an SWI image, an accentuated T1 weighted image, an MRA image (e.g., a phase contract MRA image, a time-of-flight (TOF) MRA image), or a like, or any combination thereof. Exemplary advanced images may include a virtual image, such as a virtual saturation recovery image (e.g., a virtual saturation recovery T1-weighted image), a virtual inversion recovery (IR) image (e.g., a virtual IR T1-weighted image, a virtual IR white matter (WM) nulled image, a virtual IR grey matter (GM) nulled image, a virtual IR cerebrospinal fluid (CSF) nulled image), a virtual double-IR image (e.g., a virtual double-IR WM image, a virtual double-IR GM image, a virtual double-IR image CSF image), a virtual phase sensitive inversion recovery (PSIR) image, a virtual steady state image (e.g., a virtual PD weighted image, a virtual T1 weighted image, a virtual T2* weighted image), or the like, or any combination thereof.

For illustration purposes, a measurement relating to a specific quantitative parameter is used herein to collectively refer to determining a value of the specific quantitative parameter of a physical point and/or generating a quantitative map or image relating to the specific quantitative parameter. For example, T1 measurement may be used to collectively refer to determining a T1 value of a physical point, generating a T1 map, a T1 weighted image, an accentuated T1 weighted image of the subject, or the like, or any combination thereof.

In some embodiments, the processing device 120 may perform a measurement on the subject by performing methods disclosed in examples described below. In some embodiments, the processing device 120 may perform a measurement on the subject based on a multi-dimension integration (MDI) algorithm. The MDI algorithm may integrate data in different signal dimensions in the measurement. For example, the measurement may relate to a parameter of a physical point of the subject. The processing device 120 may determine a signal representation of the physical point based on the first set and/or the second set, and determine the measurement based on the signal representation of the physical point. The signal representation may be associated with the parameter. As used herein, the signal representation may refer to a representative value or an attribute value of echo signals in the first set (or a portion of the first set) and/or the second set (or a portion of the second set). The signal representation of the subject may reflect one or more physiological characteristics or physical characteristics of the subject, which may provide a basis for medical diagnosis and/or treatment.

In some embodiments, the processing device 120 may determine a plurality of signals of the physical point based on the first set and/or the second set. As used herein, a signal of the physical point may convey information about one or more attributes or characteristics of the physical point. For example, the signals of the physical point may be or include image data or K-space data relating to the physical point. In some embodiments, the processing device 120 may reconstruct a plurality of images. Each image may be reconstructed based on an echo signal of the first set or the second set, and include image data (e.g., a pixel having a specific pixel value, a voxel having a specific voxel value) of the physical point. The processing device 120 may then designate the image data of the physical point in the images as the signals of the physical point. Each signal of the physical point may correspond to a set of values in a plurality of signal dimensions of signal acquisition using the MR scanner. A signal dimension of a signal may refer to a parameter that describes an instance under which the signal is determined or acquired using the MR scanner as described in connection with FIG. 2. Exemplary signal dimensions may include a TE, a TR, a coil unit, a repetition, a flip angle, an acquisition, or the like, or any combination thereof.

The processing device 120 may further determine a primary signal dimension and at least one secondary signal dimension among the plurality of signal dimensions. The primary signal dimension may refer to a signal dimension of the signals that is associated with the signal representation. A signal dimension may be regarded as being associated with the signal representation if the signal dimension and the signal representation have a certain mathematical correlation (e.g., an index correlation, a linear correlation, or any other mathematical correlation). The at least one secondary signal dimension may include any signal dimension of the signals other than the primary signal dimension. The at least one secondary signal dimension may include any signal dimension other than the primary signal dimension. In some embodiments, each of the secondary signal dimension may be not associated (or correlate) with the signal representation. In some embodiments, the at least one secondary signal dimension may include all or a portion of the signal dimensions of the signals other than the primary signal dimension.

The processing device 120 may further determine the signal representation of the physical point based on the plurality of signals, the primary signal dimension, and the at least one secondary signal dimension. For example, for at least one value in the at least one secondary signal dimension, the processing device 120 may determine at least one preliminary signal representation of the physical point associated with the primary signal dimension based on a portion of the plurality of signals that correspond to the value of the at least one secondary signal dimension, and determine the signal representation of the subject based on at least a portion of the at least one preliminary signal representation of the subject. As another example, the processing device may determine the signal representation of the physical point by inputting the plurality of signals into an optimization function of the signal representation, which incorporates the primary signal dimension and the at least one secondary signal dimension. More descriptions regarding the MDI algorithm may be found in, for example, U.S. application Ser. No. 16/357,313 filed Mar. 18, 2019, entitled "SYSTEMS AND METHODS FOR SIGNAL REPRESENTATION DETERMINATION IN MAGNETIC RESONANCE IMAGING," the contents of each of which are hereby incorporated by reference.

It should be noted that the above description regarding the process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 600 may be accomplished with one or more additional operations not described and/or without one or more of the operations discussed above. For example, the process 600 may include an additional operation to transmit a result of the measurement to a terminal device (e.g., a terminal device 140 of a doctor) for display.

EXAMPLES

The examples are provided for illustration purposes, and not intended to limit the scope of the present disclosure.

Example 1

Figure 8:
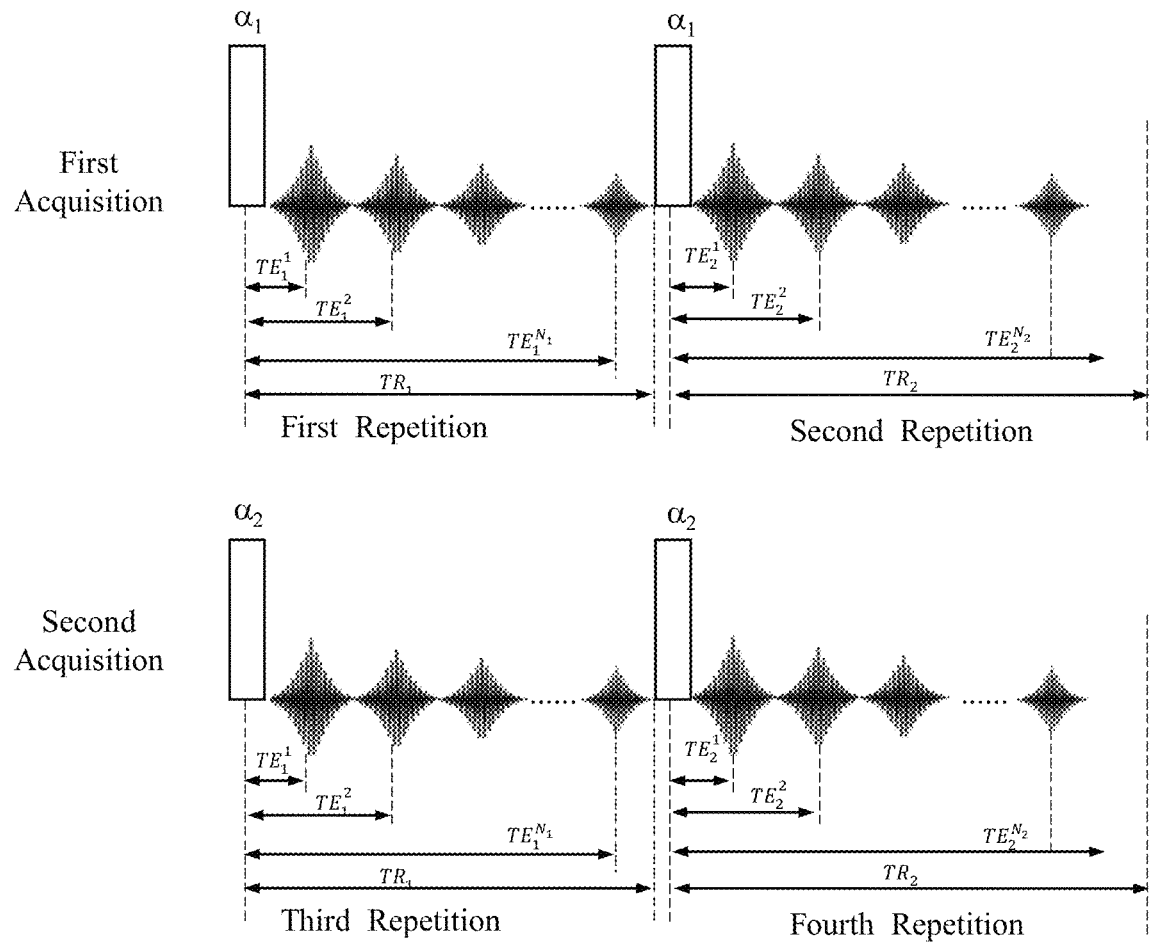

FIG. 8 is a schematic diagram illustrating an exemplary MR pulse sequence 800 according to some embodiments of the present disclosure. The MR pulse sequence 800 may be an exemplary embodiment of the MR pulse sequence 700 as described above.

As shown in FIG. 8, the MR pulse sequence 800 includes a first acquisition and a second acquisition. The first acquisition includes a first repetition and a second repetition, during each repetition an excitation pulse with a flip angle $\alpha_1$ is applied. The second acquisition includes a third repetition and a fourth repetition, during each repetition an excitation pulse with a flip angle $\alpha_2$ is applied. The flip angle $\alpha_2$ may be different from the flip angle $\alpha_1$. The repetition times of the first repetition and the third repetition are both equal to $TR_1$, and the repetition times of the second repetition and the fourth repetition are both equal to $TR_2$. $TR_2$ may be longer than $TR_1$. During each of the first and third repetitions, $N_1$ echo signals are acquired sequentially at echo times $TE_1^1, TE_1^2, \ldots,$ and $TE_1^{N_1}$. During each of the second and fourth repetitions, $N_2$ echo signals are acquired sequentially at echo times $TE_2^1, TE_2^2, \ldots,$ and $TE_2^{N_2}$. $N_2$ may be greater than $N_1$. $TE_1^1, TE_1^2, \ldots,$ and $TE_1^{N_1}$ may be equal to $TE_2^1, TE_2^2, \ldots,$ and $TE_2^{N_1}$, respectively.

In some embodiments, an MR scanner (e.g., the MR scanner 110) may be directed to execute the MR pulse sequence 800 on a subject to acquire a first set of echo signals in the first acquisition and a second set of echo signals in the second acquisition. Both of the first set and the second set may include $(N_1+N_2)*N_C$ echo signals, wherein $N_C$ may refer to a count of coil units of the MR scanner involved in acquiring echo signals that are subject to further processing as described herein. $N_C$ may have any positive value equal to or smaller than a total count of coil units of the MR scanner. For illustration purposes, it is assumed that $N_C$ is equal to 1, and both of the first set and the second set include $(N_1+N_2)$ echo signals detected by a certain coil unit of the MR scanner.

The processing device 120 may reconstruct an image based on each echo signal in the first and second sets, thus generating $2 \times (N_1+N_2)$ images. In some embodiments, each reconstructed image may include a plurality of pixels, each of which has a pixel value. A pixel value of a pixel in a reconstructed image may be a real value or a complex value including a phase component and an amplitude component. For the convenience of descriptions, $N_1$ images corresponding to the first repetition, $N_2$ images corresponding to the second repetition, $N_1$ images corresponding to the third repetition, and $N_2$ images corresponding to the fourth repetition are referred to as a first image set, a second image set, a third image set, and a fourth image set, respectively.

$$e^{-\frac{TR_1}{T_1(r)}} \text{ and } e^{-\frac{TR_2}{T_1(r)}}$$

are denoted as $E_1$ and $E_2$, respectively, wherein $T1(r)$ refers to the T1 of a physical point $P_r$ of the subject.

$S_1(\alpha_1, TE_1^i)$ representing a signal intensity of an $i^{th}$ (i being a positive integer equal to or smaller than $N_1$) echo signal at the physical point $P_r$ in the first repetition, and $S_2(\alpha_1, TE_2^k)$ representing a signal intensity of a $k^{th}$ (k being a positive integer equal to or smaller than $N_2$) echo signal at the physical point $P_r$ in the second repetition may be represented by Equation (1) and Equation (2), respectively, as below:

$$S_1(\alpha_1, TE_1^i) = M_0(r)\sin\alpha_1 e^{-\frac{TE_1^i}{T_2^*(r)}} \cdot \frac{1 - E_2 + (1 - E_1)E_2\cos\alpha_1}{1 - E_1 E_2 \cos^2\alpha_1}, \quad (1)$$

and $$S_2(\alpha_1, TE_2^k) = M_0(r)\sin\alpha_1 e^{-\frac{TE_2^k}{T_2^*(r)}} \cdot \frac{1 - E_1 + (1 - E_2)E_1\cos\alpha_1}{1 - E_1 E_2 \cos^2\alpha_1}, \quad (2)$$

where $M_0(r)$ refers to the PD of $P_r$, and $T^*_2(r)$ refers to the T2* of $P_r$. A signal intensity of an $i^{th}$ echo signal at $P_r$ in the third repetition, which is denoted as $S_1(\alpha_2, TE_1^i)$, may be represented by a similar equation as Equation (1), e.g., by replacing $\alpha_1$ with $\alpha_2$. A signal intensity of a $k^{th}$ echo signal at $P_r$ in the fourth repetition, which is denoted as $S_2(\alpha_2, TE_2^k)$, may be represented by a similar equation as Equation (2), e.g., by replacing $\alpha_1$ with $\alpha_2$.

In some embodiments, the processing device 120 may perform a T2 measurement and/or an R2 measurement on the subject. For example, a value of T2 at $P_r$ (denoted as $T_2(r)$) and/or a value of T2* at $P_r$ (denoted as $T^*_2(r)$) may be determined. Additionally or alternatively, one or more of a T2 map, a T2* map, a T2 weighted image, and a T2* weighted image of the subject may be generated. As another example, a value of R2 at $P_r$ (denoted as $R_2(r)$) and/or a value of R2* at $P_r$ (denoted as $R^*_2(r)$) may be determined. $R_2(r)$ may be a reciprocal of $T_2(r)$, and $R^*_2(r)$ may be a reciprocal of $T^*_2(r)$. Additionally or alternatively, an R2 map and/or an R2* map of the subject may be generated.

For illustration purposes, the determination of $T^*_2(r)$ is provided as an example. In some embodiments, the processing device 120 may determine $T^*_2(r)$ based on one or more of the first, second, third, and fourth image sets using a data fitting algorithm. For example, the processing device 120 may extract image data corresponding to $P_r$ from each image in the first image set corresponding to the first repetition. The image data corresponding to $P_r$ in an image may be a real pixel value or an amplitude component of a complex pixel value. The image data corresponding to $P_r$ in the images of the first image set may reflect signal intensities at $P_r$ at different TEs in the first repetition. The processing device 120 may determine $T^*_2(r)$ by fitting the image data with a fitting model (e.g., a linear fitting algorithm, an exponential fitting algorithm) of signal intensity. As another example, the processing device 120 may determine a value of $T^*_2(r)$ based on each image set according to a data fitting algorithm, respectively. The processing device 120 may determine, for example, an average value of $T^*_2(r)$ of each image set as a final value of $T^*_2(r)$.

As yet another example, the processing device 120 may determine $T^*_2(r)$ based on an MDI algorithm. In some embodiments, for each image of the $2\times(N_1+N_2)$ images, the processing device 120 may extract image data corresponding $P_r$ from the image, and designate the image data as a signal of the subject corresponding to the image. Each signal may correspond to a set of values in a plurality of signal dimensions of signal acquisition using the MR scanner. The signal dimensions may include a primary signal dimension (e.g., the TE) associated with T2* and/or at least one secondary signal dimension other than the primary signal dimension (e.g., the TR, the flip angle). The processing device 120 may determine a first signal representation of the physical point $P_r$ associated with T2* based on the primary signal dimension associated with T2* and/or the at least one secondary signal dimension. The processing device 120 may further determine $T^*_2(r)$ based on the first signal representation according to the relationship between the first signal representation and T2*.

In some embodiments, the processing device 120 may perform a B0 field measurement on the subject. For example, a local field distribution $\Delta B0(r)$ at $P_r$ may be determined, and/or a $\Delta B$ distribution map of the subject may be generated. Taking $\Delta B0(r)$ as an instance, the determination of $\Delta B0(r)$ may be performed in a similar manner as that of $T^*_2(r)$ but based on a phase component of a complex pixel value corresponding to $P_r$ in each of the $2\times(N_1+N_2)$ images (or a portion of the images). For example, the processing device 120 may determine $\Delta B0(r)$ according to a data fitting algorithm or an MDI algorithm.

Optionally, the processing device 120 may further perform a measurement relating to a tissue magnetic susceptibility on the subject based on the result of the B0 field measurement. For example, the processing device 120 may determine a quantitative susceptibility mapping (QSM) parameter (e.g., a local susceptibility field, a background susceptibility field, prior information and/or artifact information related the local susceptibility field) of $P_r$ and/or generate a quantitative susceptibility map of the subject based on $\Delta B0(r)$ and/or a $\Delta B0$ distribution map of the subject. In some embodiments, the measurement relating to the tissue magnetic susceptibility may be performed according to a QSM algorithm. Exemplary QSM algorithms may include a quantitative susceptibility and residual mapping (QUASAR) algorithm, an optimization algorithm based on Bayesian statistics. More descriptions regarding QSM algorithms may be found in, for example, U.S. application Ser. No. 16/247,098 filed on Jan. 14, 2019, entitled "METHODS AND SYSTEMS FOR DETERMINING SUSCEPTIBILITY DISTRIBUTION," and U.S. application Ser. No. 16/235,117 filed on Dec. 28, 2018, entitled "SYSTEMS AND METHODS FOR ATTENUATION CORRECTION," the contents of each of which are hereby incorporated by reference.

In some embodiments, the processing device 120 may perform a measurement relating to an actual flip angle (AFA) on the subject. For example, an AFA at $P_r$ may be determined and/or an AFA distribution map of the subject may be generated. In some occasions, B1 inhomogeneity may result in a discrepancy between an AFA at $P_r$ and a preset flip angle at $P_r$, which may further impact the accuracy of T1 mapping. Therefore, it is necessary to provide an effective method for AFA determination.

For illustration purposes, the determination of an AFA at $P_r$ in the first acquisition, which is denoted as $\alpha'_1(r)$, is provided as an instance. In some embodiments, the processing device 120 may determine $\alpha'_1(r)$ based on $S_1(\alpha_1, TE_1^i)$ (as described in Equation (1)) and $S_2(\alpha_1, TE_2^i)$ (as described in Equation (2)), wherein i may be any positive integer equal to or smaller than $N_1$. A ratio R(r) of $S_2(\alpha_1, TE_2^i)$ to $S_1(\alpha_1, TE_1^i)$ may be represented according to Equation (3) as below:

$$R(r) = \frac{S_2(\alpha_1, TE_2^i)}{S_1(\alpha_1, TE_1^i)} = \frac{1 - E_1 + (1 - E_2)E_1\cos\alpha'_1(r)}{1 - E_2 + (1 - E_1)E_2\cos\alpha'_1(r)}. \quad (3)$$

The value of $S_1(\alpha_1, TE_1^i)$ may be determined based on image data of $P_r$ in an image corresponding to the $i^{th}$ echo signal in the first repetition. $S_2(\alpha_1, TE_2^i)$ may be determined based on image data of $P_r$ in an image corresponding to the $i^{th}$ echo signal in the second repetition. Thus, a value of R(r) may be determined. Normally, $TR_1$ may be much less than $T_1(r)$, and $TR_2$ may be much less than T1(r) in an MR scan. $E_1$ and $E_2$ may be transformed according to Equation (4) and Equation (5), respectively, as below:

$$E_1 \approx 1 - \frac{TR_1}{T1(r)}, \quad (4)$$

and $$E_2 \approx 1 - \frac{TR_2}{T1(r)}. \quad (5)$$

A ratio of $TR_2$ to $TR_1$ may be denoted as n, thereby Equation (3) may be transformed according to Equation (6) as below:

$$R(r) \approx \frac{1 + n \cdot \cos\alpha'_1(r)}{n + \cos\alpha'_1(r)}. \quad (6)$$

Then, $\alpha'_1(r)$ may be determined according to Equation (7) as below:

$$\alpha'_1(r) \approx \cos^{-1}\left(\frac{R(r)*n - 1}{n - R(r)}\right). \quad (7)$$

The determination of the AFA at $P_r$ in the second acquisition (denoted as $\alpha'_2(r)$) may be performed based on $S_1(\alpha_2, TE_1^i)$ and $S_2(\alpha_2, TE_2^i)$ in a similar manner as that of $\alpha'_1(r)$.

In some embodiments, the processing device 120 may determine $\alpha'_1(r)$ of $P_r$ based on the MDI algorithm. Merely by way of an example, the processing device 120 may determine R(r), which may be regarded as a second signal representation associated with $\alpha'_1(r)$ as illustrated in Equation (7), based on the plurality of signals of $P_r$, a primary signal dimension (i.e., the actual flip angle) associated with R(r), and/or at least one secondary signal dimension (e.g., the TE, the coil unit, the acquisition, the TR) other than the primary signal dimension. For example, R(r) may be determined according to an optimization function (8) as below:

$$\operatorname{argmin}_{R(r)} \left\| \frac{S_2(\alpha_m, TE_2^i)}{S_1(\alpha_m, TE_1^i)} - R(r) \right\|^2, \quad (8)$$

where Nacq refers to a total count of acquisitions of the MR pulse sequence 800 (i.e., 2 in the example illustrated in FIG. 8). The processing device 120 may determine R(r) by solving the optimization function (8), and further determine $\alpha'_1(r)$ based on R(r) and Equation (7).

In some embodiments, a ratio of $\alpha'_1(r)$ to $\alpha_1$ may be determined to measure a system error of the MR scanner, for example, the larger the difference of the ratio from 1 is, the bigger the system error is. Additionally or alternatively, the processing device 120 may further perform a B1 transmission field measurement on the subject based on the measurement result relating to the AFA. For example, the processing device 120 may determine a B1 transmission field at $P_r$ (denoted as B1(r)) and/or generate a B1 transmission field distribution map of the subject based on a linear correlation between actual flip angles and B1 transmission fields.

In some embodiments, the processing device 120 may perform a T1 measurement on the subject. For example, a value of T1 at $P_r$ (denoted as $T_1(r)$) may be determined. Additionally or alternatively, a T1 map and/or a T1 weighted image of the subject may be generated. In some embodiments, the processing device 120 may determine at least one of an AFA or a B1 transmission field relating to the subject based on the first set and/or the second set. The processing device 120 may further perform the T1 measurement based on the first set, the second set, and the at least one of the AFA or the B1 transmission field relating to the subject.

Taking $T_1(r)$ as an example, the processing device 120 may determine $\alpha'_1(r)$ and $\alpha'_2(r)$ based on the first set and/or the second set as described above. The processing device 120 may determine $T_1(r)$ based on the first set, the second set, $\alpha'_1(r)$, and $\alpha'_2(r)$. For example, $T_1(r)$ may be determined based on $S_1(\alpha'_1(r), TE_1^i)$ and $S_1(\alpha'_2(r), TE_1^i)$. A ratio R'(r) may be represented according to Equation (9), as below:

$$R'(r) = \frac{S_1(\alpha'_1(r), TE_1^i)\sin\alpha'_2(r)}{S_1(\alpha'_2(r)TE_1^i)\sin\alpha'_1(r)} = \quad (9)$$

$$\frac{1 - E_2 + (1 - E_1)E_2\cos\alpha'_1(r)}{1 - E_1E_2\cos^2\alpha'_1(r)} \cdot \frac{1 - E_1E_2\cos^2\alpha'_2(r)}{1 - E_2 + (1 - E_1)E_2\cos\alpha'_2(r)}.$$

A ratio of $TR_1$ to T1(r) may be denoted as K, and Equation (9) may be transformed based on the Equations (4) and (5) according to Equation (10) as below:

$$R'(r) \approx \frac{n + \cos\alpha'_1(r) + nK\cos\alpha'_1(r)}{\sin^2\alpha'_1(r) + (n+1)K\cos^2\alpha'_1(r)} \cdot \frac{\sin^2\alpha'_2(r) + (n+1)K\cos^2\alpha'_2(r)}{n + \cos\alpha'_2(r) + nK\cos\alpha'_2(r)}. \quad (10)$$

The value of $S_1(\alpha'_1(r), TE_1^i)$ may be determined based on image data of $P_r$ in an image corresponding to the $i^{th}$ echo signal in the first repetition. The value of $S_1(\alpha'_2(r), TE_1^i)$ may be determined based on image data of $P_r$ in an image corresponding to the $i^{th}$ echo signal in the third repetition. Thus, a value of R'(r) may be determined. Equation (10) may be regarded as a quadratic equation with one unknown parameter (i.e., K), therefore Equation (10) may be transformed into Equation (11) as below:

$$aK^2 + bK + c = 0, \quad (11)$$

where a, b, and c may be determined according to Equations (12)-(14) as below:

$$a = n(n+1)\cos\alpha'_2(r)\cos\alpha'_2(r)(R'(r)\cos\alpha'_1(r) - \cos\alpha'_2(r)), \quad (12)$$

$$b = (n+1)(n\cos^2\alpha'_2(r) - nR'(r)\cos^2\alpha'_1(r) + \cos\alpha'_1(r)\cos^2\alpha'_2(r) - R'(r)\cos^2\alpha'_1(r)\cos\alpha'_2(r)) + n(R'(r)\sin^2\alpha'_1(r)\cos\alpha'_2(r) - \cos\alpha'_1(r)\sin^2\alpha'_2(r)), \quad (13)$$

and $$c = \sin^2\alpha'_2(r)(n + \cos\alpha'_1(r)) - R'(r)\sin^2\alpha'_1(r)(n + \cos\alpha'_2(r)), \quad (14)$$

The values of K and $T_1(r)$ may be determined according to Equations (15) and (16), respectively, as below:

$$K = \frac{-b \pm \sqrt{b^2 - 4ac}}{2a}, \quad (15)$$

and $$T_1(r) = \frac{2aTR_1}{-b \pm \sqrt{b^2 - 4ac}}. \quad (16)$$

In some embodiments, K may be equal to $$\frac{-b - \sqrt{b^2 - 4ac}}{2a}$$

and $T_1(r)$ may be equal to $$\frac{2aTR_1}{-b - \sqrt{b^2 - 4ac}}.$$

As another example, $T_1(r)$ may be determined based on $S_2(\alpha'_1(r), TE_2^k)$ and $S_2(\alpha'_2(r), TE_2^k)$ in a similar manner as it is determined based on $S_1(\alpha'_1(r), TE_2^i)$ and $S_1(\alpha'_2(r), TE_2^i)$. In such cases, $S_1(\alpha'_1(r), TE_1^i)$ and $S_1(\alpha'_2(r), TE_1^i)$ in Equations (9) and (10) may be replaced by $S_2(\alpha'_1(r), TE_2^k)$ and $S_2(\alpha'_2(r), TE_2^k)$, respectively. Equation (10) may be transformed into Equation (17) as below:

$$a'K^2 + b'K + c' = 0. \quad (17)$$

where a', b', and c' may be determined according to Equations (18)-(20) as below:

$$a' = n(n+1)\cos \alpha'_1(r)\cos^2\alpha'_2(r)(R'(r)\cos \alpha'_1(r) - \cos \alpha'_2(r)), \quad (18)$$

$$b' = (n+1)(\cos^2 \alpha'_2(r) - R'(r)\cos^2 \alpha'_1(r) + n \cos \alpha'_1(r)\cos^2 \alpha'_2(r) - nR'(r)\cos^2 \alpha'_1(r)\cos \alpha'_2(r)) - n(R'(r)\sin^2 \alpha'_1(r)\cos \alpha'_2(r) - \cos \alpha'_1(r)\sin^2 \alpha'_2(r)), \quad (19)$$

and $$c' = -\sin^2 \alpha'_2(r)(1+n \cos \alpha'_1(r)) + R'(r)\sin^2 \alpha'_1(r)(1+n \cos \alpha'_2(r)), \quad (20)$$

The value of $T_1(r)$ may be determined according to Equations (21) as below:

$$T_1(r) = \frac{2a'TR_1}{-b' \pm \sqrt{b'^2 - 4a'c'}}. \quad (21)$$

In some embodiments, $T_1(r)$ may be equal to $$\frac{2a'TR_1}{-b' - \sqrt{b'^2 - 4a'c'}}.$$

Theoretically, the value of $T_1(r)$ determined according to Equation (16) may be equal to or substantially equal to the value of $T_1(r)$ determined according to Equation (21). The processing device 120 may determine the value of $T_1(r)$ according to Equation (16) or (21). Alternatively, the processing device 120 may determine two values of $T_1(r)$ according to Equations (16) and (21), respectively, and further determine an average value of the two values as a final value of $T_1(r)$.

In some embodiments, the processing device 120 may determine $T_1(r)$ based on the MDI algorithm. Merely by way of example, the processing device 120 may determine R'(r), which may be regarded as a third signal representation associated with $T_1(r)$, based on the plurality of signals of $P_r$, a primary signal dimension (i.e., the flip angle) associated with R'(r), and/or at least one secondary signal dimension (e.g., the TE, the coil unit, the acquisition, the TR) other than the primary signal dimension. In some embodiments, R'(r) may be determined according to an optimization function (22) as below:

$$\operatorname{argmin}_{R'(r)} \sum_{m=1}^{N_{acq}} \sum_{i=1}^{N_m} \left\| \frac{S_m(\alpha'_1(r), TE_m^i)\sin\alpha'_2(r)}{S_m(\alpha'_2(r), TE_m^i)\sin\alpha'_1(r)} - R'(r) \right\|^2. \quad (22)$$

The processing device 120 may determine R'(r) by solving the optimization function (22), and further determine $T_1(r)$ based on R'(r) and one or more of the Equations (11)-(21).

In some embodiments, the processing device 120 may perform a PD measurement on the subject. For example, a value of PD at $P_r$ (denoted as $M_0(r)$) may be determined and/or a PD distribution map of the subject may be generated. For illustration purposes, the determination of $M_0(r)$ is described as an example. $M_0(r)$ may be determined by transforming Equation (1) according to Equation (23) or by transforming Equation (2) according to Equation (24) as below:

$$M_0(r) = \frac{S_1(\alpha_m, TE_1^i)(1 - E_1E_2\cos^2\alpha_m)}{(1 - E_2 + (1 - E_1)E_2\cos\alpha_m)\sin\alpha_m e^{-\frac{TE_1^i}{T_2^*(r)}}} \approx \quad (23)$$

$$\frac{S_1(\alpha_m, TE_1^i)(\sin^2\alpha_m - (n+1)K\cos^2\alpha_m)}{K(n + \cos\alpha_m - nK\cos\alpha_m)\sin\alpha_m e^{-\frac{TE_1^i}{T_2^*(r)}}}, \text{ and}$$

$$M_0(r) = \frac{S_2(\alpha_m, TE_2^k)(1 - E_1E_2\cos^2\alpha_m)}{(1 - E_1 + (1 - E_2)E_1\cos\alpha_m)\sin\alpha_m e^{-\frac{TE_1^k}{T_2^*(r)}}} \approx \quad (24)$$

$$\frac{S_2(\alpha_m, TE_2^k)(\sin^2\alpha_m - (n+1)K\cos^2\alpha_m)}{K(1 + n\cos\alpha_m - nK\cos\alpha_m)\sin\alpha_m e^{-\frac{TE_2^k}{T_2^*(r)}}},$$

where m may be equal to 1 or 2.

Theoretically, the value of $M_0(r)$ determined according to Equation (23) may be equal to or substantially equal to the value of $M_0(r)$ determined according to Equation (24). The processing device 120 may input the determined K (i.e., $TR_1/T1(r)$) and $T^*_2(r)$ into Equation (23) or (24) to determine a value of $M_0(r)$. Alternatively, the processing device 120 may determine two values of $M_0(r)$ according to Equations (23) and (24), respectively, and further determine, for example, an average value of the two values as a final value of $M_0(r)$.

In some embodiments, the processing device 120 may perform a water measurement and/or a fat measurement on the subject. For example, a water fraction and/or a fat fraction at $P_r$ may be determined. Additionally or alternatively, a fat-water separated image, such as a water-only image (also referred to as a fat-suppressed image) and/or a fat-only image of the subject may be generated.

For illustration purposes, the generation of the fat-water separated image is described as an example. In some embodiments, the processing device 120 may generate the fat-water separated image on the echo signals acquired in one repetition. Alternatively, the processing device 120 may generate a plurality of fat-water separated images, each of which is generated based on the echo signals in one repetition. The processing device 120 may determine an average image of the plurality of fat-water separated images as a final fat-water separated image.

In some embodiments, the processing device 120 may generate a fat-water separated image according to a fat-water imaging algorithm, e.g., a Dixon algorithm, an iterative decomposition of water and fat with echo asymmetry and least-squares estimation (IDEAL) algorithm, a Flex algorithm, a multi-point Dixon (mDixon) algorithm, a Fat-Sep algorithm, a water-fat opposed phase (WFOP) algorithm, or the like, or any combination thereof. For example, the fat-water separated image may be generated based on the echo signals acquired in the first repetition according to the Dixon algorithm. The excitation pulse in the first repetition may excite echo signals at specific TEs to achieve the measurement relating to water and/or fat. The echo signals with specific TEs may include a first echo signal at a first TE with water and fat signals in-phase and a second echo signal at a second TE with water and fat signals 180° out-of-phase. The processing device 120 may generate an image $I_1$ with water and fat signals in-phase based on the first echo signal and an image $I_2$ with water and fat signals 180° out-of-phase based on the second echo signal. The processing device 120 may further determine $0.5*(I_1+I_2)$ as the water-only image and/or $0.5*(I_1-I_2)$ as the fat-only image. In some embodiments, the water measurement and/or the fat measurement may be performed based on the MDI algorithm.

In some embodiments, the processing device 120 may perform a measurement relating to one or more virtual images of the subject. Each virtual image of the subject may correspond to a specific MR pulse sequence, and refer to an image that is derived from a result of one or more other measurements performed on the subject without actually applying the specific MR pulse sequence on the subject. For example, a first virtual image may correspond to a GRE pulse sequence having a virtual flip angle $\upsilon\alpha$, a virtual echo time $\upsilon$TE, and a virtual repetition time $\upsilon$TR. A pixel value of $P_r$ in the first virtual image, which is denoted as $\upsilon S1(r)$, may be determined according to Equation (25) as below:

$$\upsilon S1(r) = \frac{M_0(r)(1 - \upsilon E_1)\sin(\upsilon\alpha)e^{-\frac{\upsilon TE}{T_2^*(r)}}}{1 - \upsilon E_1 \cos(\upsilon\alpha)}, \quad (25)$$

where $M_0(r)$ and $T_2^*(r)$ may be determined according to exemplary methods described above, and $\upsilon$TE may be equal to $$e^{-\frac{\upsilon TR}{T_1(r)}}.$$

As another example, a second virtual image may correspond to an IR pulse sequence having a virtual echo time $\upsilon$TE and a virtual inversion time $\upsilon$TI. A pixel value of $P_r$ in the second virtual image, which is denoted as $\upsilon S2(r)$, may be determined according to Equation (26) as below:

$$\upsilon S2(r) = M_0(r)\left|1 - 2e^{-\frac{\upsilon TI}{T_1(r)}}\right|e^{-\frac{\upsilon TE}{T_2^*(r)}}. \quad (26)$$

As another example, a third virtual image may correspond to a saturation recovery pulse sequence having a virtual echo time $\upsilon$TE and a virtual inversion time $\upsilon$TI. A pixel value of $P_r$ in the third virtual image, which is denoted as $\upsilon S3(r)$, may be determined according to Equation (27) as below:

$$\upsilon S3(r) = M_0(r)\left(1 - e^{-\frac{\upsilon TI}{T_1(r)}}\right)e^{-\frac{\upsilon TE}{T_2^*(r)}}. \quad (27)$$

As another example, a fourth virtual image may correspond to a phase sensitive inversion recovery (PSIR) pulse sequence having a virtual echo time $\upsilon$TE and a virtual inversion time $\upsilon$TI. A pixel value of $P_r$ in the fourth virtual image, which is denoted as $\upsilon S4(r)$, may be determined according to Equation (28) as below:

$$\upsilon S4(r) = M_0(r) \cdot \mathrm{sign}\left(1 - 2e^{-\frac{\upsilon TI}{T_1(r)}}\right)\left|1 - 2e^{-\frac{\upsilon TI}{T_1(r)}}\right|e^{-\frac{\upsilon TI}{T_2^*(r)}}, \quad (28)$$

where sign represents a mathematical function that extracts the sign of a real number.

As another example, a fifth virtual image may correspond to a steady state pulse sequence having a virtual flip angle $\upsilon\alpha$, a virtual echo time $\upsilon$TE, a virtual inversion time $\upsilon$TI, and a virtual repetition time $\upsilon$TR. A pixel value of $P_r$ in the fifth virtual image, which is denoted as $\upsilon S5(r)$, may be determined according to Equation (29) as below:

$$\upsilon S5(r) = M_0(r)\frac{1 - e^{-\frac{\upsilon TR}{T_1(r)}}}{1 - e^{-\frac{\upsilon TI}{T_1(r)}}\cos(\upsilon\alpha)}\sin(\upsilon\alpha). \quad (29)$$

In some embodiments, the processing device 120 may generate a virtual phase map of the subject corresponding to $\upsilon$TE of the GRE pulse sequence described above. For example, a virtual phase at $P_r$ and $\upsilon$TE in the virtual phase map, denoted as $\varphi(r)$, may have a linear correlation with $\Delta B0(r)$. Merely by way of example, $\varphi(r)$ may be equal to $\Delta B0(r) \times \gamma \times \upsilon TE$, wherein $\gamma$ refers to a gyromagnetic ratio. The virtual phase map corresponding to $\upsilon$TE may be determined by determining a virtual phase of each physical point.

Optionally, the processing device 120 may further generate a susceptibility weighted imaging (SWI) image of the subject based on the virtual phase map and the echo signals acquired in one or more of the repetitions. For example, a phase mask may be based on the virtual phase map, and a magnitude image of the subject may be generated based on the echo signals acquired in one or more of the repetitions. The SWI image of the subject may be generated based on the phase map and the magnitude map. In some embodiments, the SWI image may be generated according to an SWI algorithm, such as a susceptibility weighted angiography (SWAN) algorithm, an SWI-phase (SWIp) algorithm, a blood sensitive imaging (BSI) algorithm, a flow-sensitive black blood (FSBB) algorithm, or the like. More descriptions regarding SWI technique may be found in, for example, U.S. Application No. 2018/0017652 A1 filed on May 13, 2017 and U.S. Patent No. 2018/0231631 A1 filed on Jul. 14, 2016, both entitled "SYSTEM AND METHOD FOR MAGNETIC RESONANCE IMAGING," the contents of each of which are hereby incorporated by reference.

In some embodiments, the processing device 120 may further generate an accentuated T1 weighted image of the subject. For example, the processing device 120 may generate an accentuated T1 weighted image of the subject corresponding to the $i^{th}$ echo signal in the first repetition detected by a certain coil unit. Assuming that $\alpha_2$ is larger than $\alpha_1$, a pixel value of $P_r$ in the accentuated T1 weighted image may be determined according to Equation (30) as below:

$$S_{aT1W}(r) = \frac{S_1(\alpha_2, TE_1^i)}{S_1(\alpha_1, TE_1^i)}, \qquad (30)$$

where $S_{aT1W}(r)$ refers to the pixel value of $P_r$ in the accentuated T1 weighted image.

In some embodiments, $S_{aT1W}(r)$ may be determined based on the MDI algorithm according to an optimization function (31) as below:

$$\mathrm{argmin}_{S_{aT1W}(r)} \sum_{m=1}^{Nacq} \sum_{i=1}^{N_m} \left\| \frac{S_m(\alpha_2, TE_m^i)}{S_m(\alpha_1, TE_m^i)} - S_{aT1W}(r) \right\|^2. \qquad (31)$$

As another example, the processing device 120 may generate an accentuated T1 weighted image corresponding to each echo signal in each repetition detected by each coil unit. The processing device 120 may further generate an average image of the accentuated T1 weighted images as an accentuated T1 weighted image of the subject corresponding to the whole scan. As yet another example, the processing device 120 may generate the accentuated T1 weighted image of the subject corresponding to the whole scan according to the MDI algorithm. For example, the processing device 120 may determine $S_{aT1W}(r)$, which may be regarded as a fourth signal representation associated with the flip angle, based on the plurality of signals of $P_r$, a primary signal dimension (i.e., the flip angle) associated with $S_{aT1W}(r)$, and/or at least one secondary signal dimension (e.g., the TE, the coil unit, the acquisition, the TR) other than the primary signal dimension.

Example 2

Figure 9:
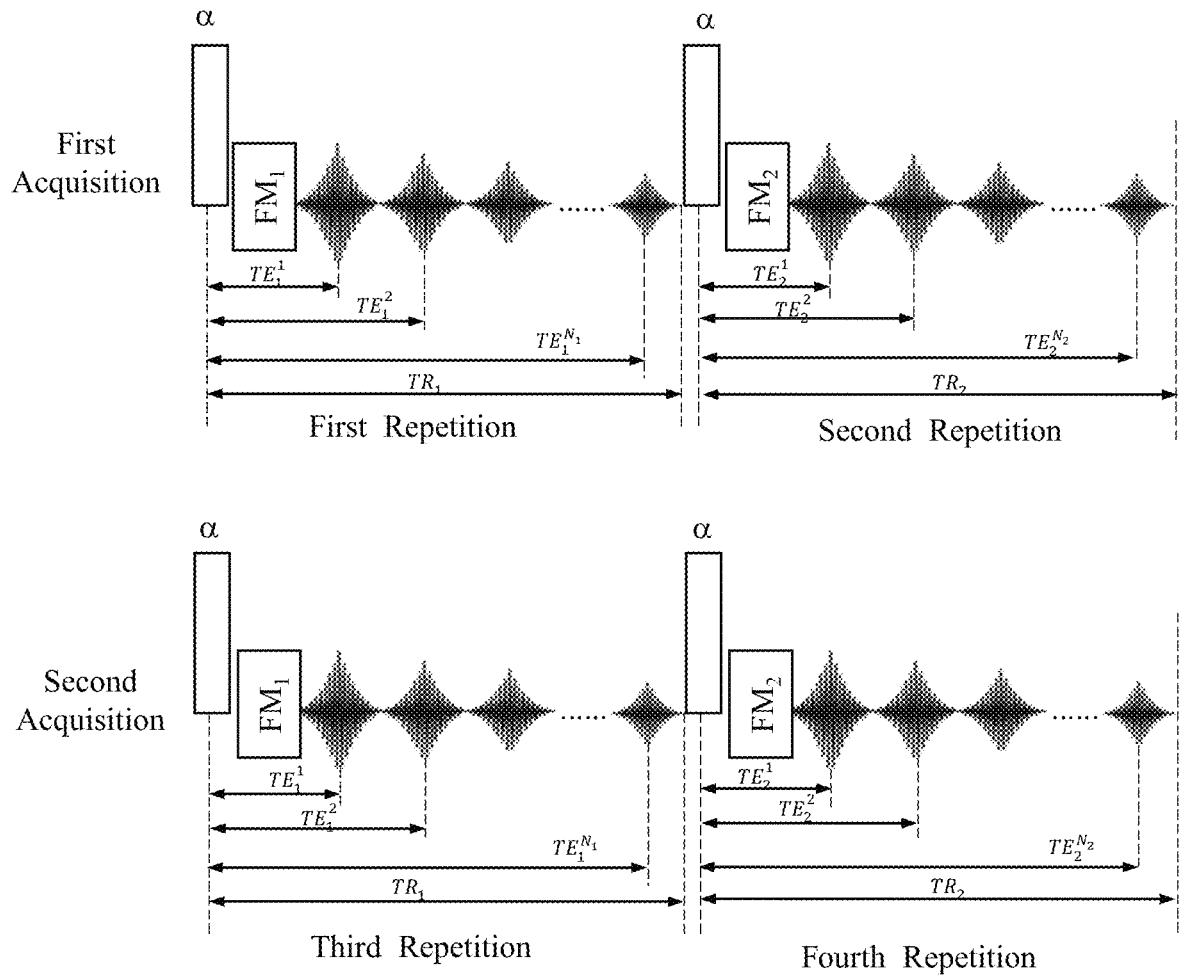

FIG. 9 is a schematic diagram illustrating an exemplary MR pulse sequence 900 according to some embodiments of the present disclosure. The MR pulse sequence 900 may be an exemplary embodiment of the MR pulse sequence 700 as described above.

The MR pulse sequence 900 may have a similar structure as the MR pulse sequence 800 except for certain components or features. As shown in FIG. 9, the flip angle of the excitation pulse of each repetition in the first acquisition and second acquisition may both be equal to $\alpha$. Each of the first repetition and the third repetition may include an FM module $FM_1$. Each of the second repetition and the fourth repetition may include an FM module $FM_2$ different from $FM_1$. For example, $FM_1$ may be an FC module and $FM_2$ may be an FD module. The signal intensity of a body fluid at a certain echo time in the first repetition (or the third repetition) may be higher than that at the certain echo time in the second repetition (or the fourth repetition). As another example, $FM_1$ may be a positive FE module and $FM_2$ may be a negative FE module. The body fluid in the first and third repetitions may have a positive phase, and the body fluid in the second and fourth repetitions may have a negative phase.

Similar to the MR pulse sequence 800, the MR pulse sequence 900 may be applied to a subject to acquire a first set of echo signals in the first acquisition and a second set of echo signals in the second acquisition. For illustration purposes, it is assumed that the first set and the second set both include $(N_1+N_2)$ echo signals acquired by a certain coil unit of the MR scanner. In some embodiments, the processing device 120 a measurement relating to an MR angiography (MRA) image on the subject based on at least one of the first set or the second set. For example, the processing device 120 may generate at least one first image of the subject based on a first portion of echo signals in the first set and/or the second set. The first portion of echo signals may include one or more echo signals acquired in the first repetition and/or the third repetition. The processing device 120 may generate at least one second image of the subject based on a second portion of echo signals in the first set and/or the second set. The second portion of echo signals may include one or more echo signals acquired in the second repetition and/or the fourth repetition. The processing device 120 may generate one or more MRA images of the subject based on the at least one first image and the at least one second image.

For illustration purposes, it is assumed that the at least one first image includes $2N_1$ images and the at least one second image includes $2N_2$ images. The $2N_1$ images include $N_1$ images (denoted as $I_1, \ldots,$ and $I_{N_1}$) corresponding to the first repetition and $N_1$ images (denoted as $I_{N_1+1}, \ldots,$ and $I_{2N_1}$) corresponding to the third repetition. The $2N_2$ images include $N_2$ images (denoted as $I'_1, \ldots,$ and $I'_{N_2}$) corresponding to the second repetition and $N_2$ images (denoted as $I'_{N_2+1}, \ldots,$ and $I'_{2N_2}$) corresponding to the fourth repetition.

The processing device 120 may generate an MRA image corresponding to a specific TE based on the first image and the second image corresponding to the specific TE. Merely by way of example, a contract enhanced MRA image corresponding to $TE_1^i$ may be generated based on $I_i$ and $I'_i$ (or $I_{2i}$ and $I'_{2i}$) by, for example, using a subtraction technique (e.g., a linear subtraction technique or a non-linear subtraction technique) in which statistic tissue may be subtracted out. In some embodiments, the processing device 120 may generate the MRA image using the MDI algorithm based on all or a portion of the $2(N_1+N_2)$ images. For example, the processing device 120 may determine an MRA image corresponding to the whole scan, which may be regarded as a fifth signal representation associated with the flow modulation type, based on the plurality of signals of each pixel, a primary signal dimension (i.e., the flow modulation type) associated with the MRA image, and/or at least one secondary signal dimension (e.g., the FA, the coil unit, the acquisition, the TR) other than the primary signal dimension.

In some embodiments, the processing device 120 may perform one or more other measurements on the subject based on the first set and/or the second set of echo signals. For example, measurements relating to T2, T2*, R2, R2*, B0 field, B1 field, actual flip angle, water, fat, QSM, etc., or a combination thereof may be performed on the subject in a similar manner as described in Example 1. However, measurements relating to T1 and PD may be unable to be performed because the measurements relating to T1 and PD may need to be performed based on echo signals corresponding to different flip angles according to relevant descriptions in Example 1.

Example 3

Figure 10:
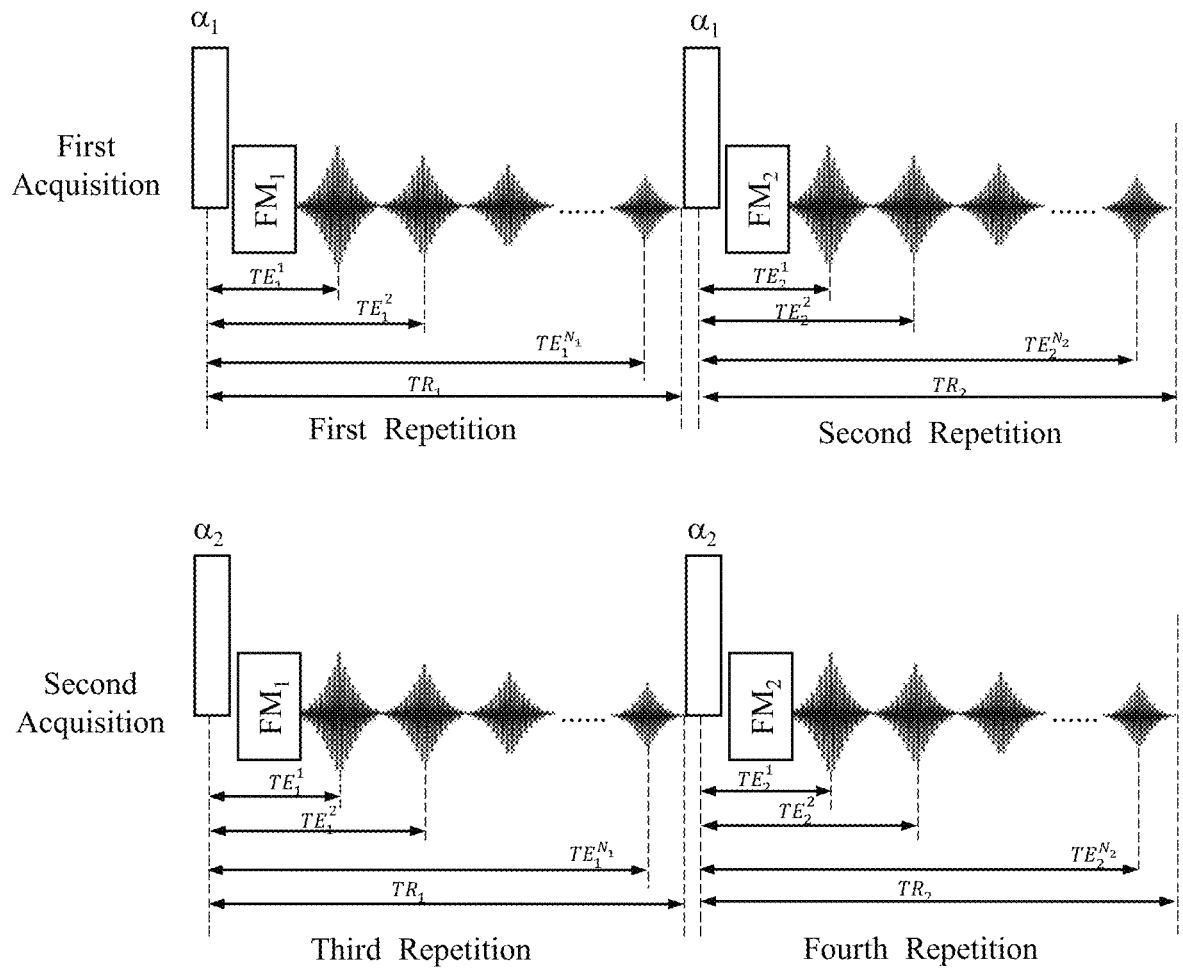

FIG. 10 is a schematic diagram illustrating an exemplary MR pulse sequence 1000 according to some embodiments of the present disclosure. The MR pulse sequence 1000 may be an exemplary embodiment of the MR pulse sequence 700 as described above.

The MR pulse sequence 1000 may have a similar structure as the MR pulse sequence 900 except for certain components or features. As shown in FIG. 10, the excitation pulses of the first and second repetitions in the first acquisition may both have a flip angle $\alpha_1$, and the excitation pulses of the third and fourth repetitions in the second acquisition may both have a flip angle $\alpha_2$ different from $\alpha_1$.

In some embodiments, the MR pulse sequence 1000 may be applied to a subject to acquire a first set of echo signals in the first acquisition and a set of echo signals in the second acquisition. The processing device 120 may perform a measurement relating to one or more of T2, T2*, R2, R2*, B0 field, B1 field, actual flip angle, T1, PD, water, fat, QSM, etc., based on the first set and/or the second set in a similar manner as described in the Example 1. Additionally or alternatively, the processing device 120 may perform a measurement relating to an MRA image on the subject in a similar manner as described in Example 2.

Example 4

Figure 11:
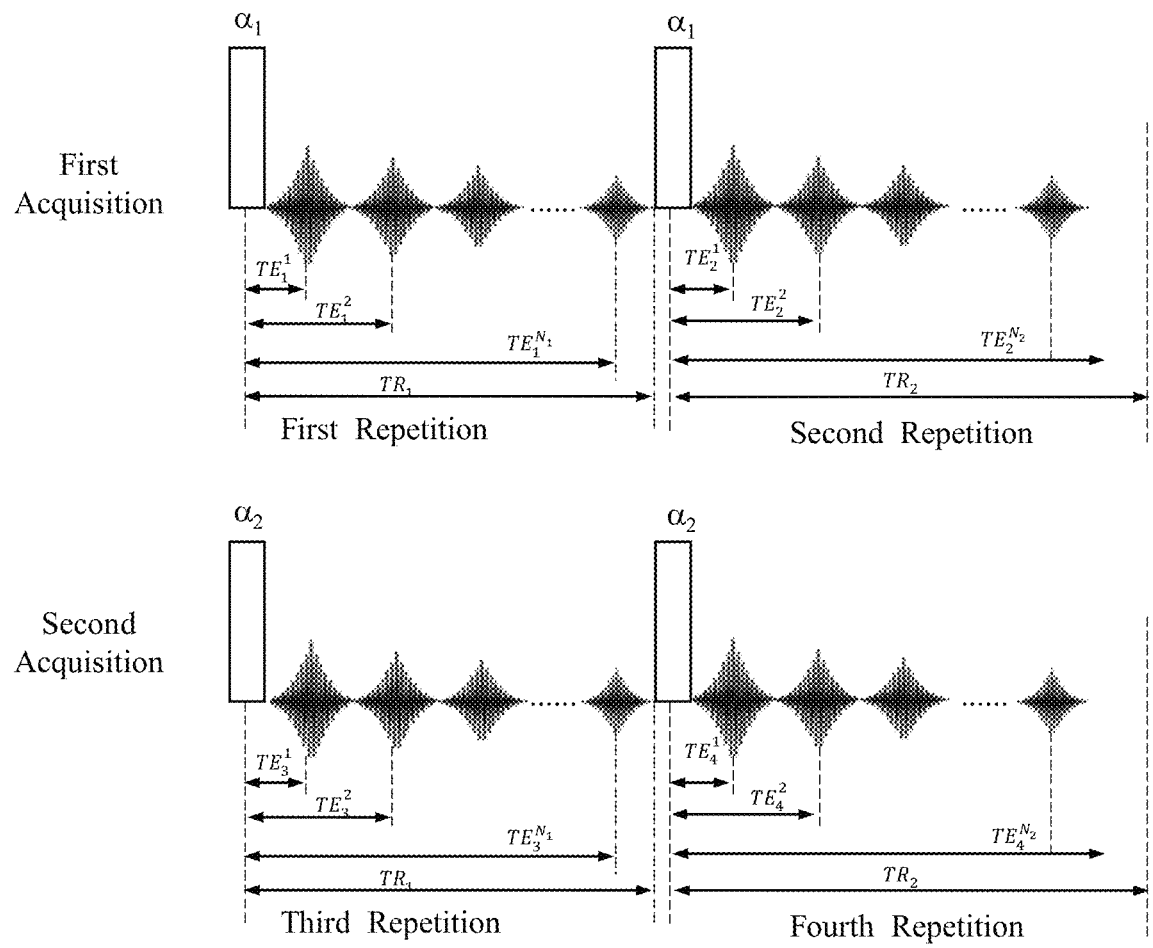

FIG. 11 is a schematic diagram illustrating an exemplary MR pulse sequence 1100 according to some embodiments of the present disclosure. The MR pulse sequence 1100 may be an exemplary embodiment of the MR pulse sequence 700 as described above.

The MR pulse sequence 1100 includes a first acquisition and a second acquisition. The first acquisition of the MR pulse sequence 1100 has a same configuration as the first acquisition of the MR pulse sequence 800. The second acquisition of the MR pulse sequence 1100 has a similar configuration as the second acquisition of the MR pulse sequence 800 except for certain components or features. As shown in FIG. 11, the second acquisition of the MR pulse sequence 1100 includes a third repetition and a fourth repetition. During the third repetition, $N_1$ echo signals are acquired sequentially at echo times $TE_3^1$, $TE_3^2$ . . . , and $TE_3^{N_1}$. $TE_3^1$ may be different $TE_1^1$, $TE_3^2$ may be different from $TE_1^2$, . . . , and $TE_3^{N_1}$ may be different from $TE_1^{N_1}$. During the fourth repetition, $N_2$ echo signals are acquired sequentially at echo times $TE_4^1$, $TE_4^2$, . . . , and $TE_4^{N_2}$, respectively. $TE_4^1$ may be different $TE_2^1$, $TE_4^2$ may be different from $TE_2^2$, . . . , and $TE_4^{N_2}$ may be different from $TE_2^{N_2}$.

In some embodiments, the MR pulse sequence 1100 may be applied to a subject to acquire a first set of echo signals in the first acquisition and a set of echo signals in the second acquisition. The processing device 120 may perform a measurement relating to one or more of T2, T2*, R2, R2*, B0 field, B1 field, actual flip angle, T1, PD, water, fat, QSM, etc., on the subject in a similar manner as described in Example 1. Additionally or alternatively, the processing device 120 may perform a measurement relating to an MRA image on the subject in a similar manner as described in Example 2.

In some embodiments, compared with MR pulse sequence 800, the MR pulse sequence 1100 using different TEs in the first and third repetitions and different TEs in the second and fourth repetitions may provide more suitable data for the measurement relating to water and/or fat. For example, as described in connection with Example 1, echo signals at specific TEs may be excited to achieve the measurement relating to water and/or fat. The echo signals with specific TEs may include a first echo signal at a first TE with water and fat signals in-phase and a second echo signal at a second TE with water and fat signals 180° out-of-phase. The time difference between the first TE and the second TE may be short (e.g., shorter than a time period), making that it is difficult to acquire the first and second echo signals in a single acquisition. The MR pulse sequence 1100 may be used to acquire the first echo signal at the first TE in an acquisition and the second echo signal at the second TE in the other acquisition, thereby achieving the measurement relating to water and/or fat.

It should be noted that the above examples illustrated in FIGS. 7 to 11 and the descriptions thereof are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, an MR pulse sequence (any one of 700 to 1100) may include one or more additional components and/or one or more components of the MR pulse sequence described above may be omitted. In addition, the Equations and optimization functions provided herein are illustrative examples and can be modified in various ways. For example, an Equation or an optimization function may include one or more other parameters and/or one or more parameters illustrated above may be omitted or replaced by other parameter(s). In some embodiments, an optimization function of a signal representation may incorporate one or more other second signal dimension(s).

FIGS. 12A to 41C illustrate exemplary measurement results of the brain of a patient according to some embodiments of the present disclosure. The measurement results were generated based on an MR pulse sequence that has a similar configuration as the MR pulse sequence 1000 and exemplary methods disclosed herein.

Figure 12A:
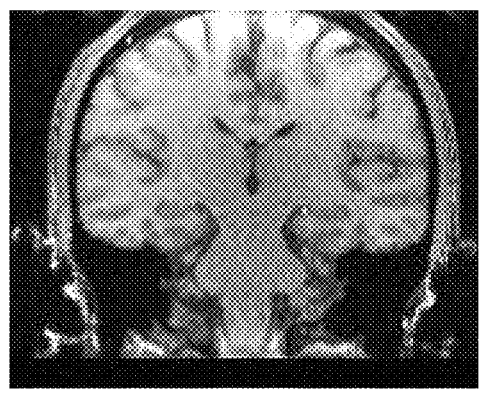
FIGS. 12A to 41C illustrate exemplary measurement results of the brain of a patient according to some embodiments of the present disclosure.
Figure 12B:
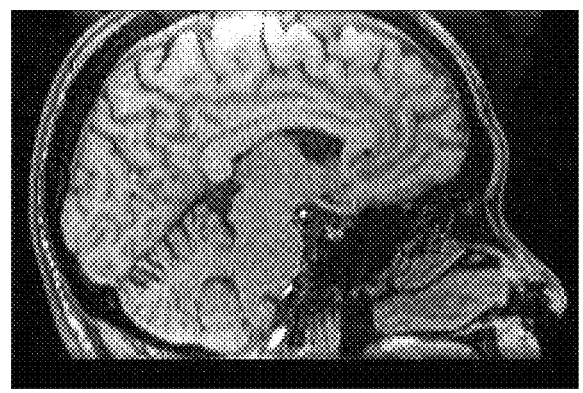
Figure 12C:
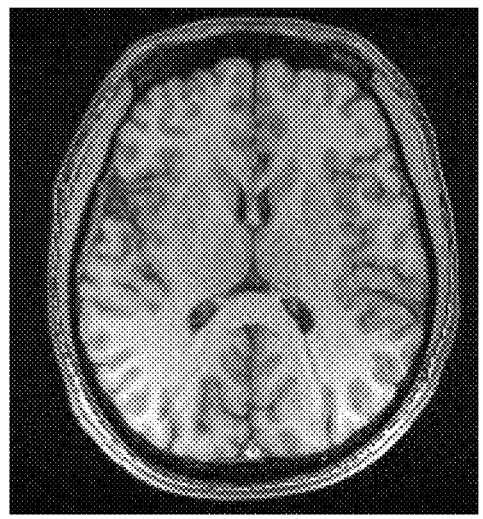
Figure 13A:
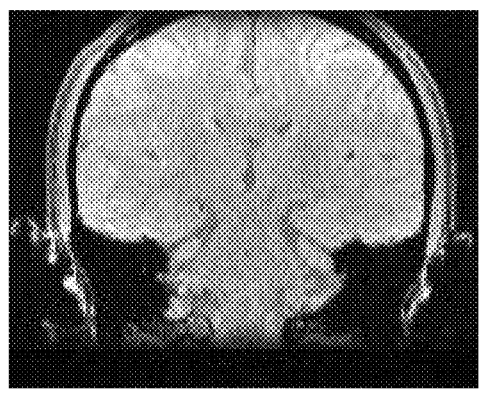
Figure 13B:
Figure 13C:
Figure 14A:
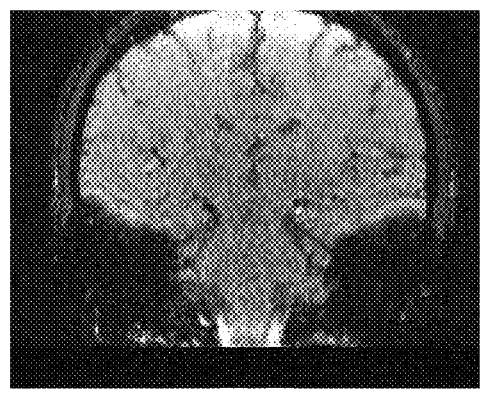
Figure 14B:
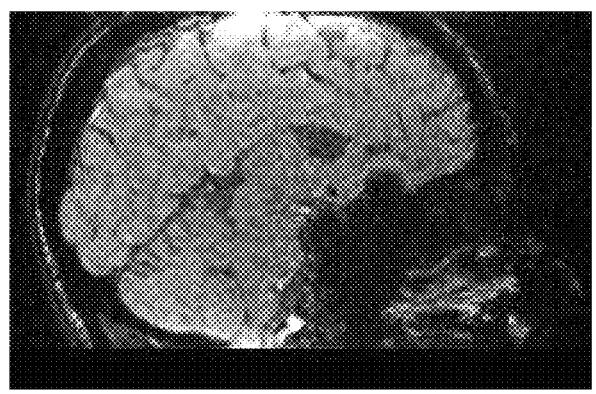
Figure 14C:
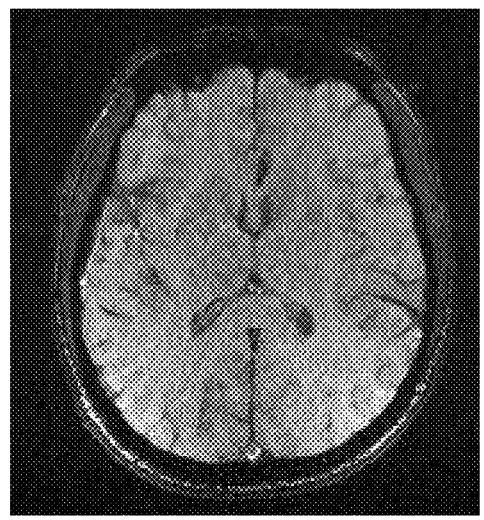
Figure 15A:
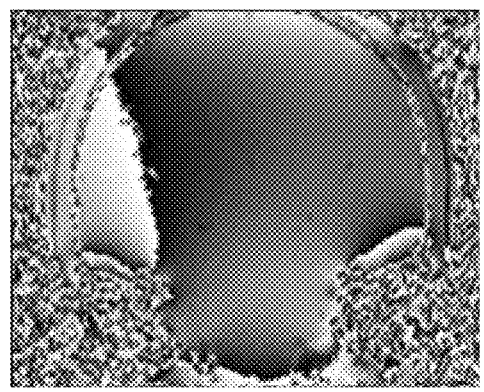
Figure 15B:
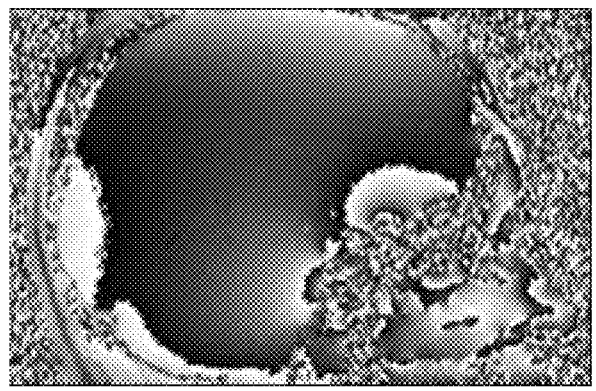
Figure 15C:
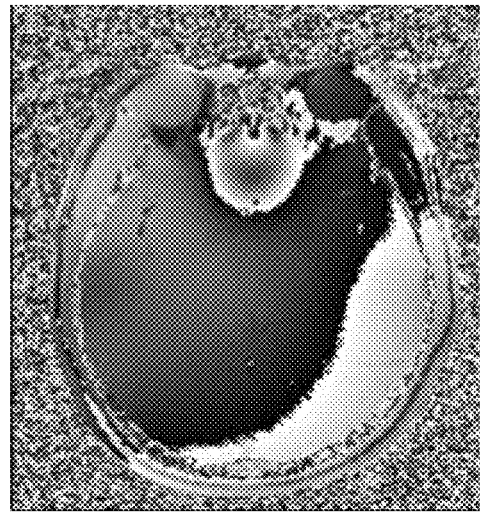
Figure 16A:
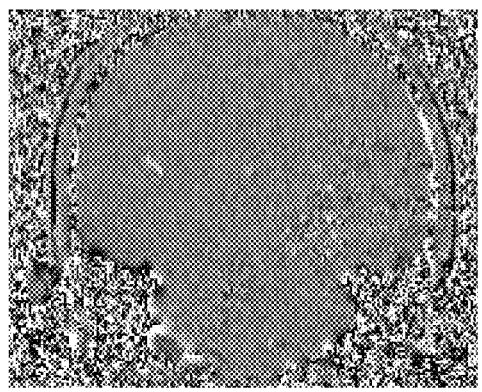
Figure 16B:
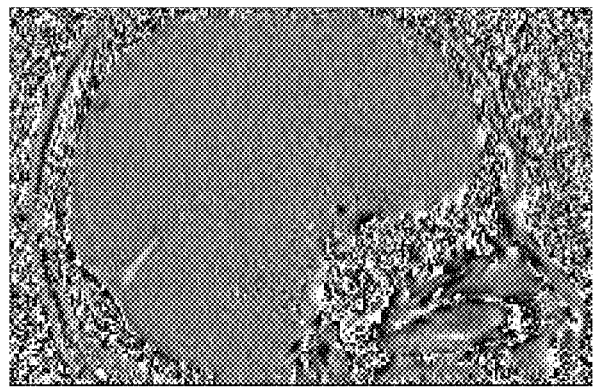
Figure 16C:
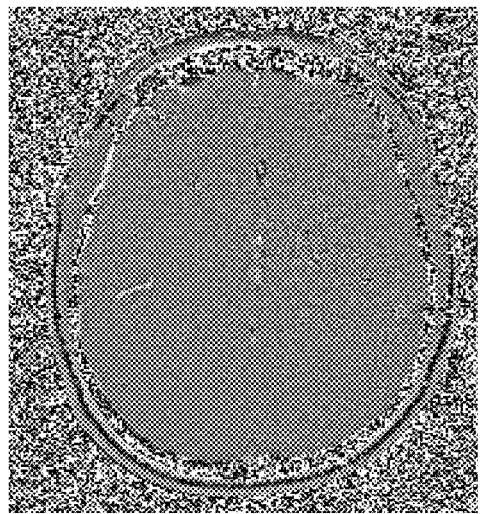
Figure 17A:
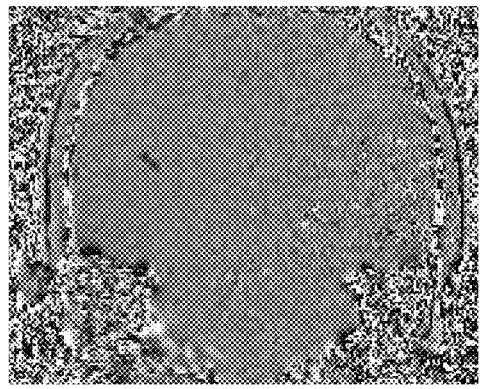
Figure 17B:
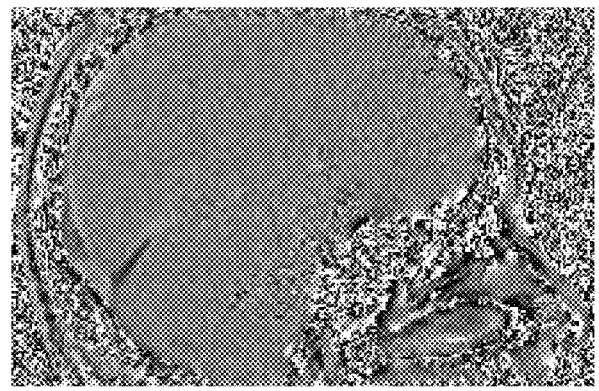
Figure 17C:
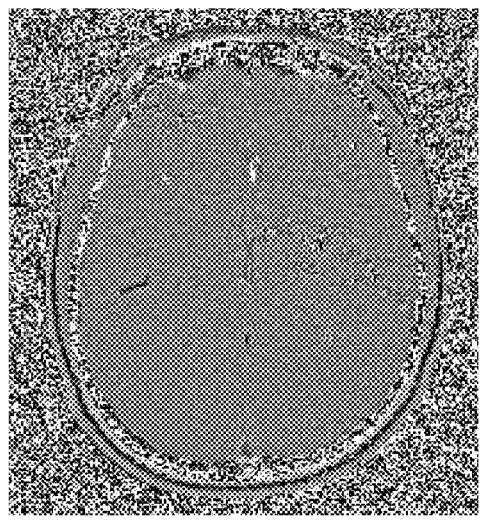

FIGS. 12A to 17C illustrate basic images of the brain. FIGS. 12A to 12C illustrate a T1 weighted image of a coronal plane, a sagittal plane, and a transverse plane of the brain, respectively. FIGS. 13A to 13C illustrate a PD weighted image of the coronal plane, the sagittal plane, and the transverse plane of the brain, respectively. FIGS. 14A to 14C illustrate a T2* weighted image of the coronal plane, the sagittal plane, and the transverse plane of the brain, respectively. FIGS. 15A to 15C illustrate a phase image of the coronal plane, the sagittal plane, and the transverse plane of the brain, respectively. FIGS. 16A to 16C illustrate a phase contrast MRA image of the coronal plane, the sagittal plane, and the transverse plane of the brain, respectively, wherein the phase contrast MRA images in FIGS. 16A to 16C were generated by using an MR pulse sequence incorporating a positive FE module. FIGS. 17A to 17C illustrate phase contrast MRA image of the coronal plane, the sagittal plane, and the transverse plane of the brain, respectively, wherein the phase contrast MRA images in FIG. 17A to 17C were generated by using an MR pulse sequence incorporating a negative FE module. Each of FIGS. 16A to 17C may be a phase image containing phase information and correspond to a complex image that includes the phase information and also amplitude information.

Figure 18A:
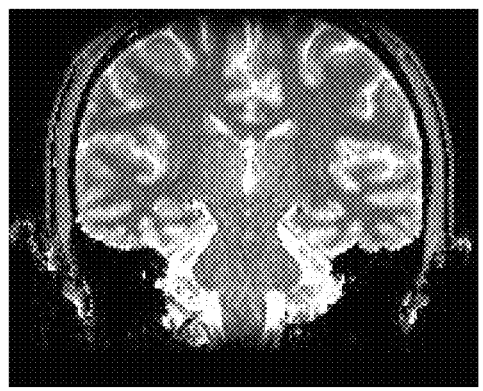
Figure 18B:
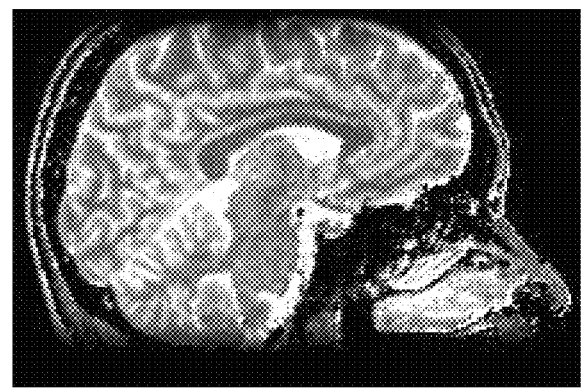
Figure 18C:
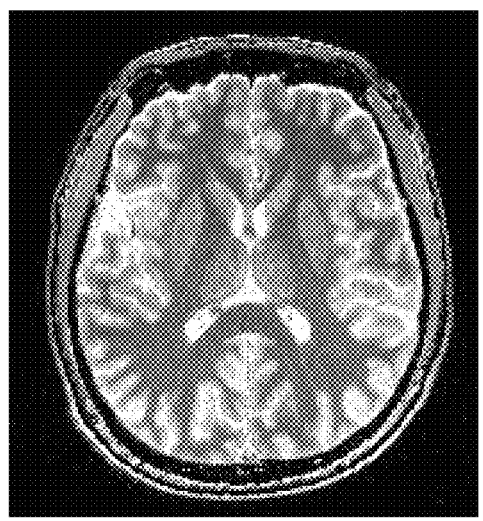
Figure 19A:
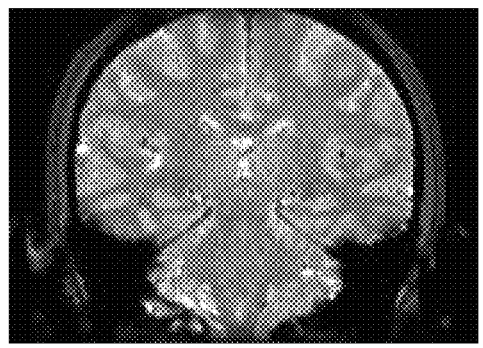
Figure 19B:
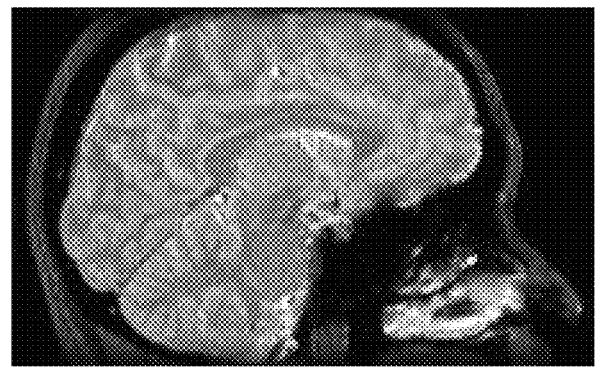
Figure 19C:
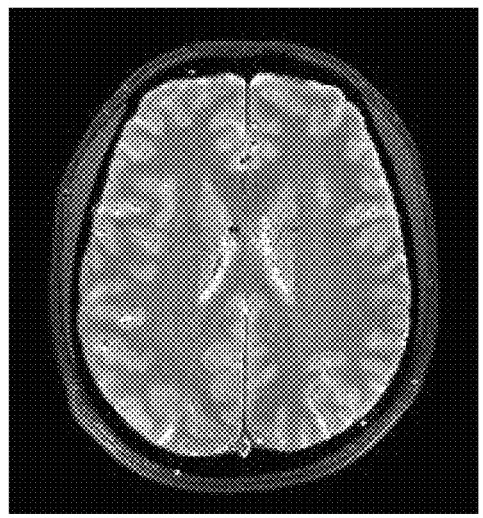
Figure 20A:
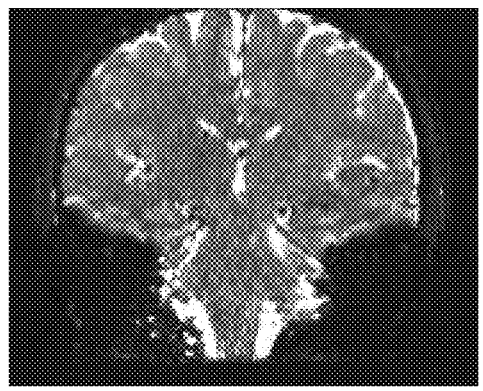
Figure 20B:
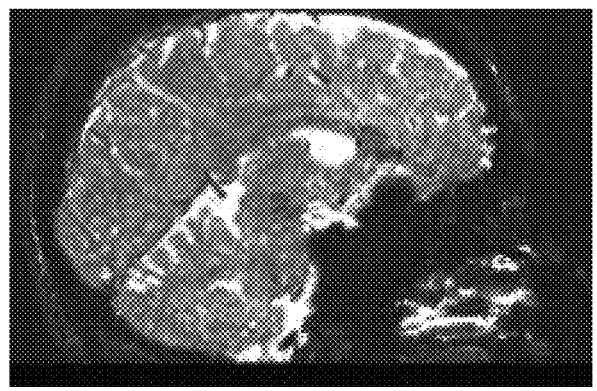
Figure 20C:
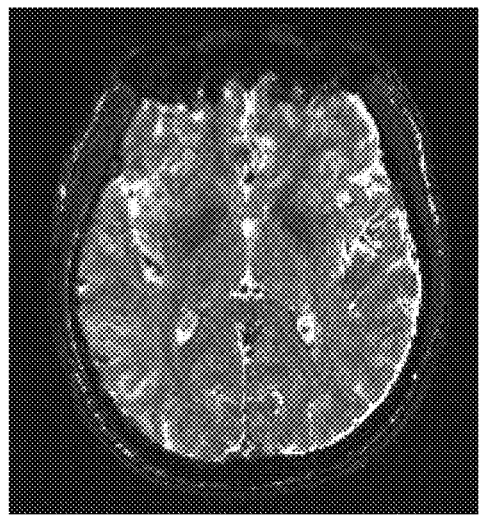
Figure 21A:
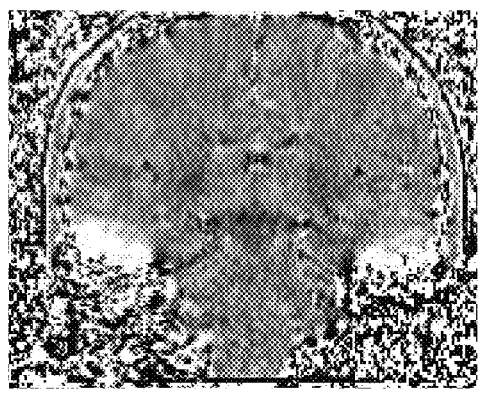
Figure 21B:
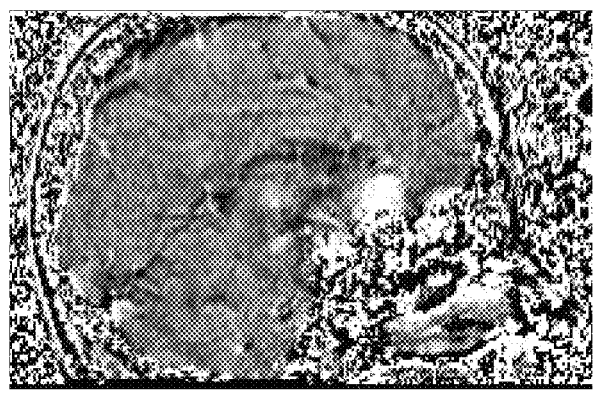
Figure 21C:
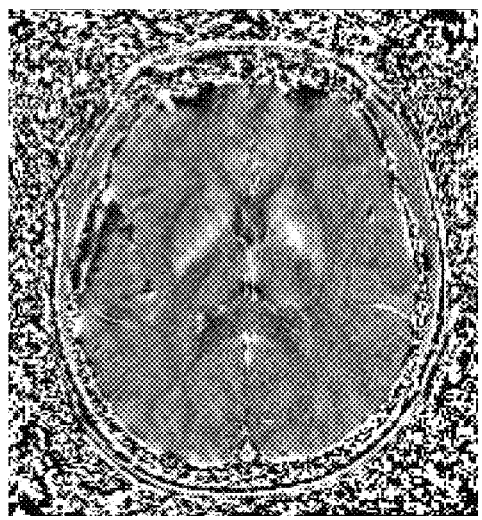
Figure 22A:
Figure 22B:
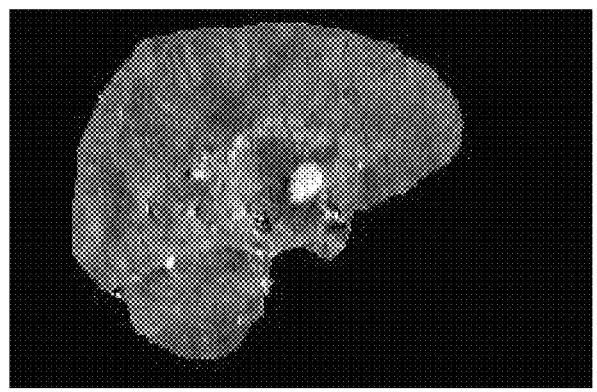
Figure 22C:
Figure 23A:
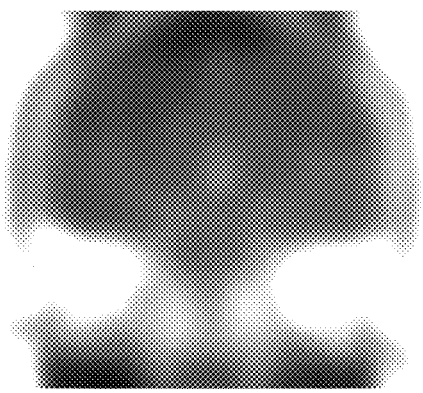
Figure 23B:
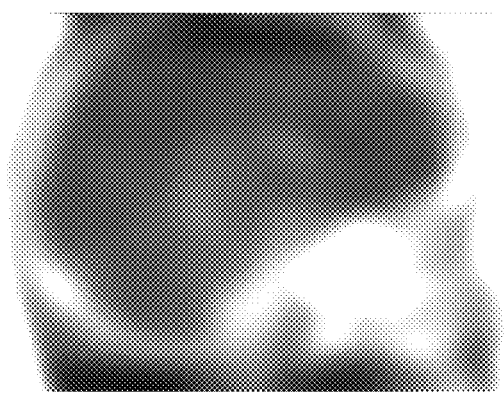
Figure 23C:
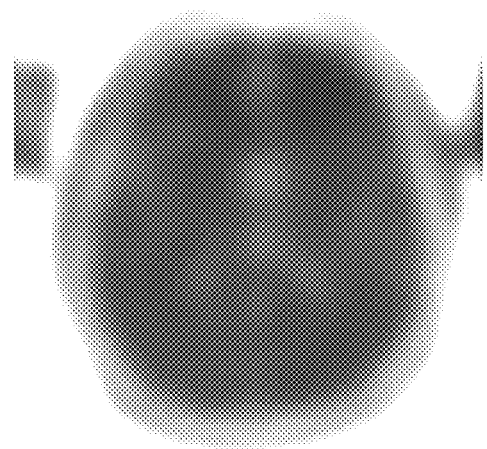
Figure 24A:
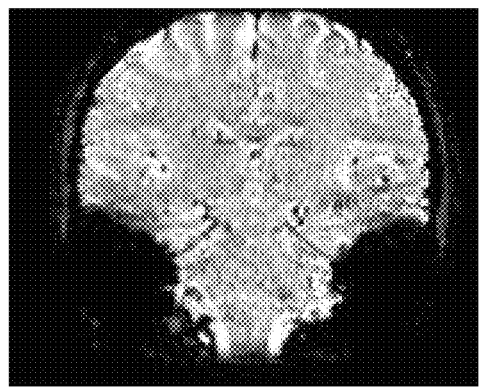
Figure 24B:
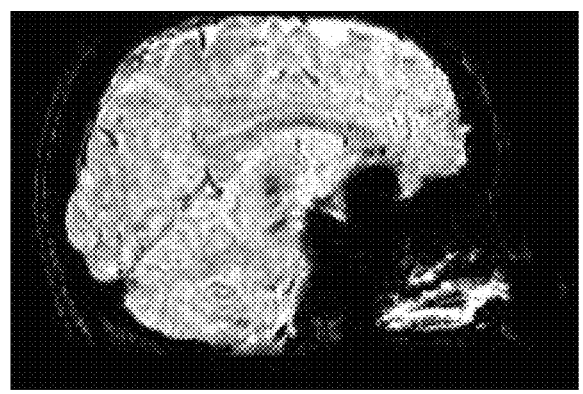
Figure 24C:
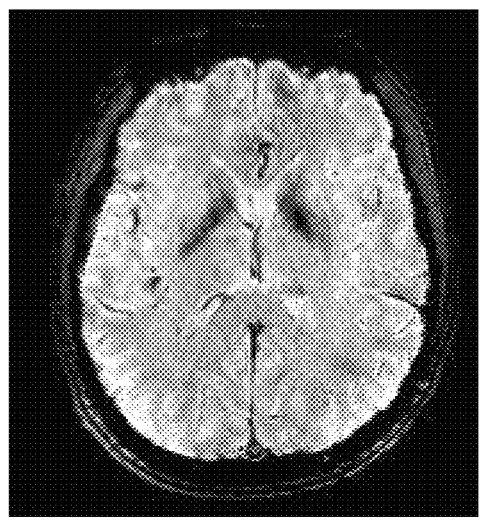
Figure 25A:
Figure 25B:
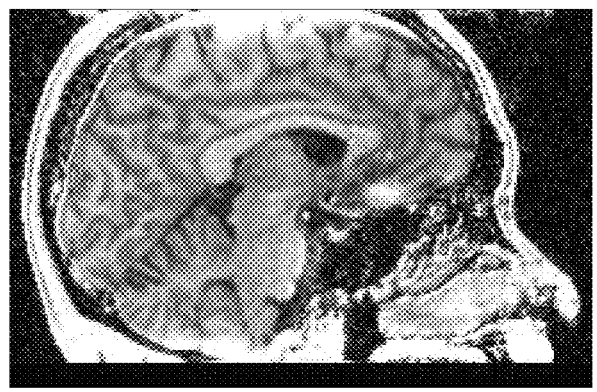
Figure 25C:
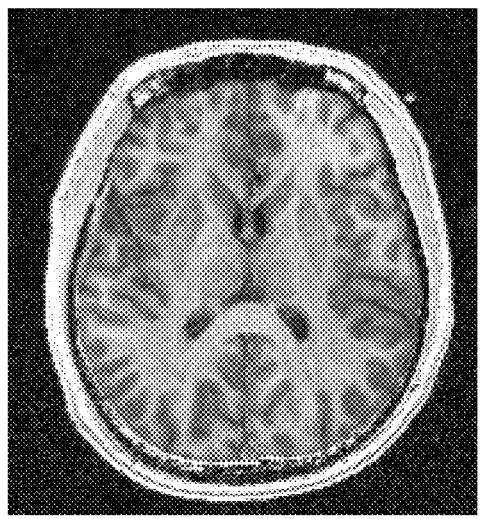
Figure 26A:
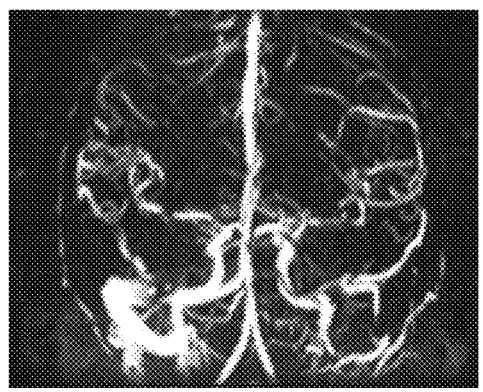
Figure 26B:
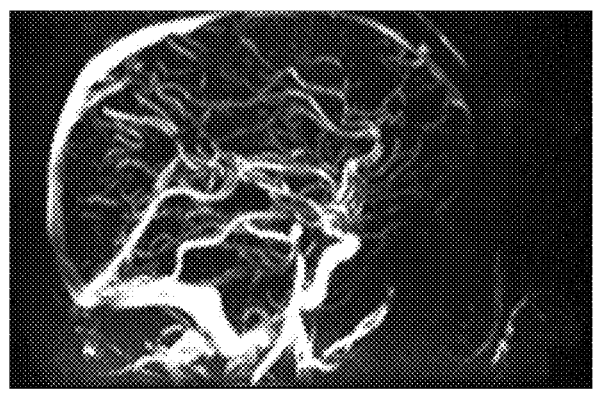
Figure 26C:
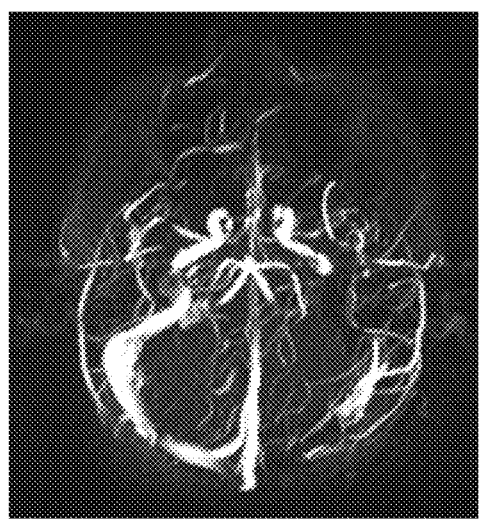
Figure 27A:
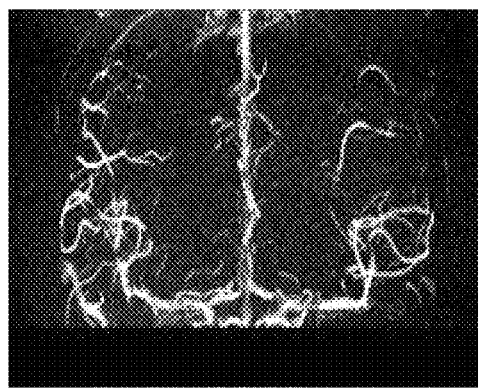
Figure 27B:
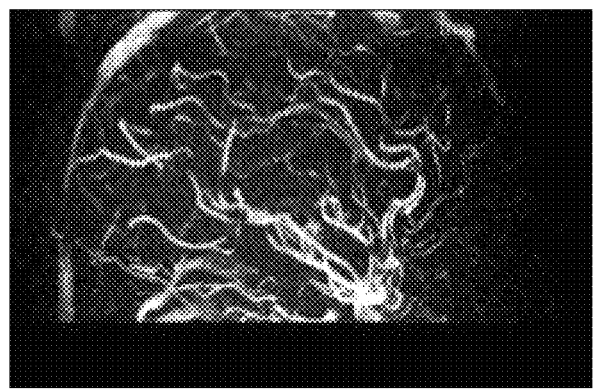
Figure 27C:
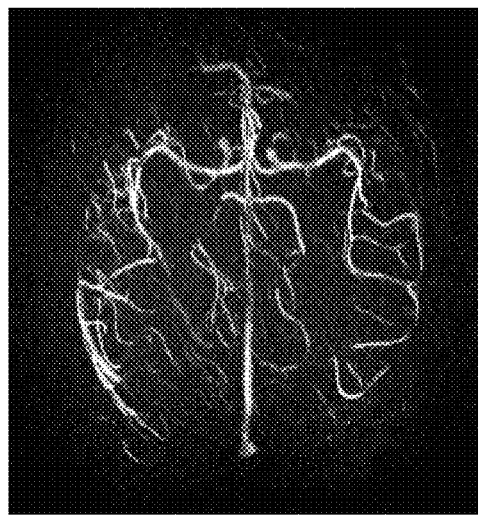
Figure 28A:
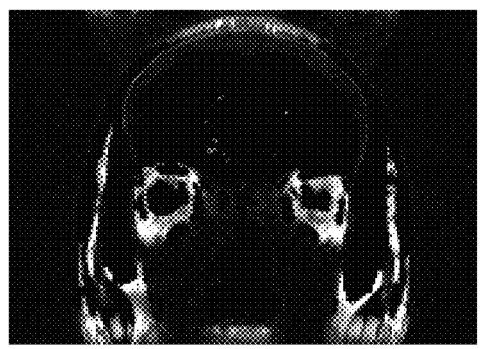
Figure 28B:
Figure 28C:
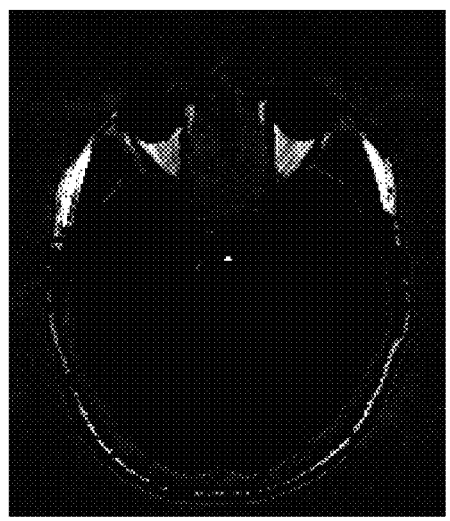
Figure 29A:
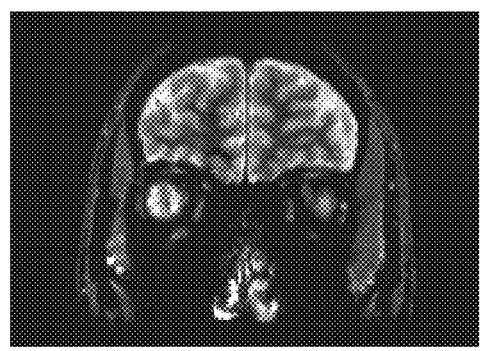
Figure 29B:
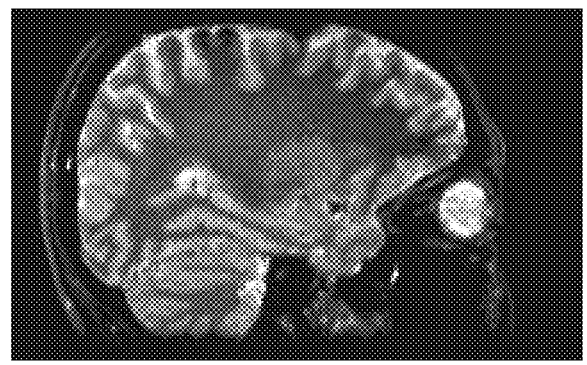
Figure 29C:
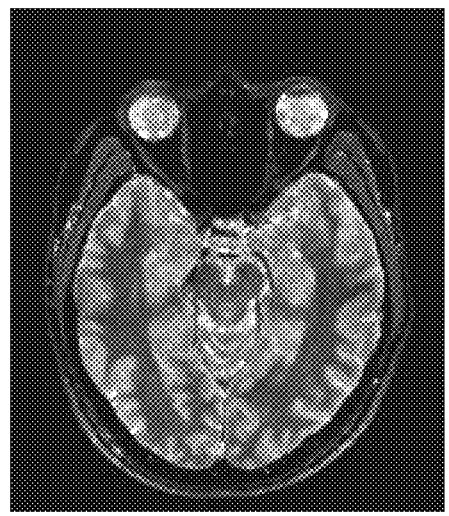
Figure 30A:
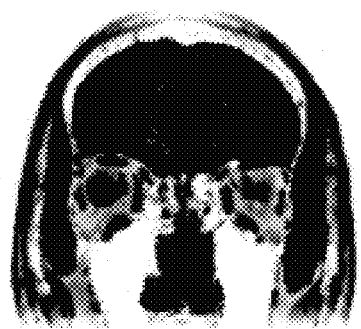
Figure 30B:
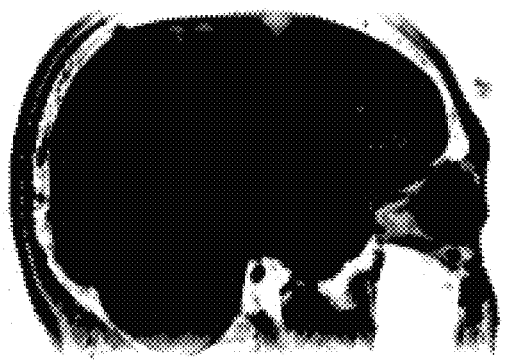
Figure 30C:

FIGS. 18A to 30C illustrate preliminary images of the brain. FIGS. 18A to 18C illustrate a T1 map of the coronal plane, the sagittal plane, and the transverse plane of the brain, respectively. FIGS. 19A to 19C illustrate a PD distribution map of the coronal plane, the sagittal plane, and the transverse plane of the brain, respectively. FIGS. 20A to 20C illustrate a T2* map of the coronal plane, the sagittal plane, and the transverse plane of the brain, respectively. FIGS. 21A to 21C illustrate a local B0 field distribution map of the coronal plane, the sagittal plane, and the transverse plane of the brain, respectively. FIGS. 22A to 22C illustrate a QS map of the coronal plane, the sagittal plane, and the transverse plane of the brain, respectively. FIGS. 23A to 23C illustrate a B1 field distribution map of the coronal plane, the sagittal plane, and the transverse plane of the brain, respectively. FIGS. 24A to 24C illustrate an SWI image of the coronal plane, the sagittal plane, and the transverse plane of the brain, respectively. FIGS. 25A to 25C illustrate an accentuated T1 weighted image of the coronal plane, the sagittal plane, and the transverse plane of the brain, respectively. FIGS. 26A to 26C illustrate a phase contracted MRA image of the coronal plane, the sagittal plane, and the transverse plane of the brain, respectively, wherein the phase contract MRA images in FIG. 26A to 26C were generated based on the complex images corresponding to the phase contract MRA images illustrated in FIGS. 16A to 17C. For example, the phase contract MRA image in FIG. 26A was generated by subtracting the complex image corresponding to the phase contract MRA image illustrated in FIG. 17A from the complex image corresponding to the phase contract MRA image illustrated in FIG. 16A. FIGS. 27A to 27C illustrate a TOF MRA image of the coronal plane, the sagittal plane, and the transverse plane of the brain, respectively. FIGS. 28A to 28C illustrate a fat-only image of the coronal plane, the sagittal plane, and the transverse plane of the brain, respectively. FIGS. 29A to 29C illustrate a water-only image of the coronal plane, the sagittal plane, and the transverse plane of the brain, respectively. FIGS. 30A to 30C illustrate a fat fraction distribution map of the coronal plane, the sagittal plane, and the transverse plane of the brain, respectively.

Figure 31A:
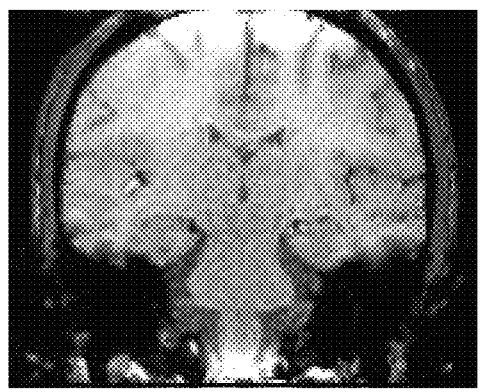
Figure 31B:
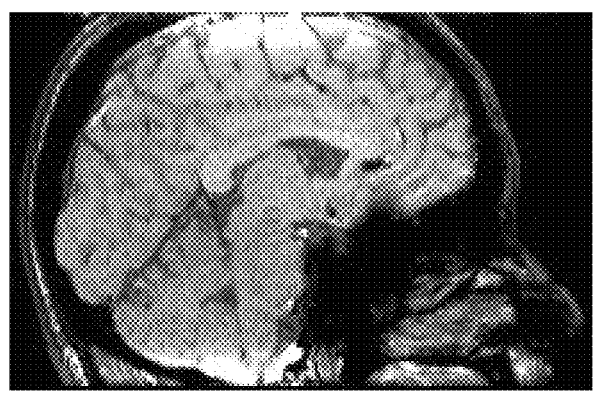
Figure 31C:
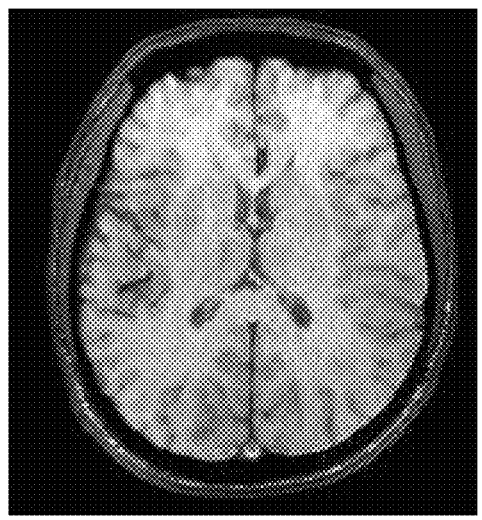
Figure 32A:
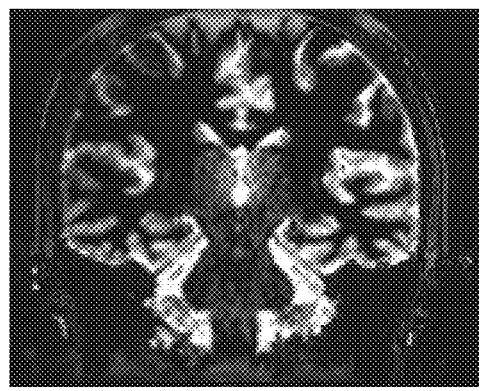
Figure 32B:
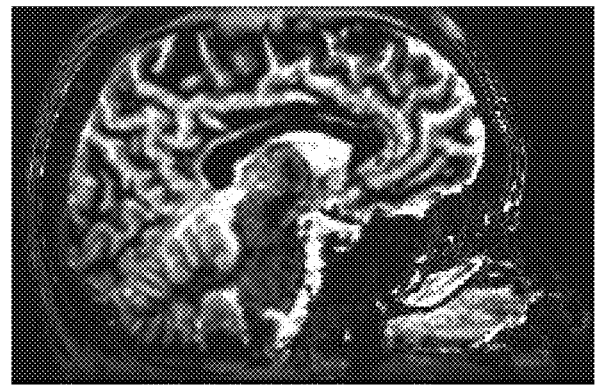
Figure 32C:
Figure 33A:
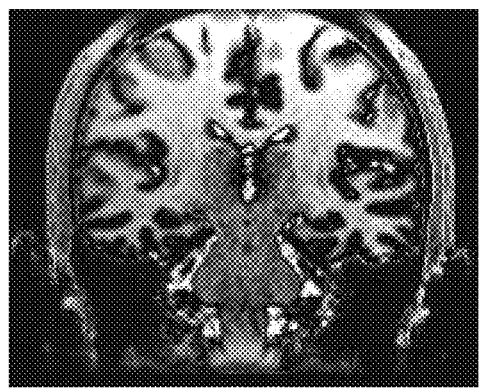
Figure 33B:
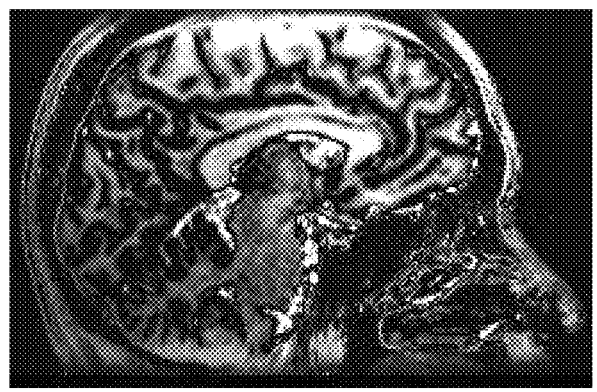
Figure 33C:
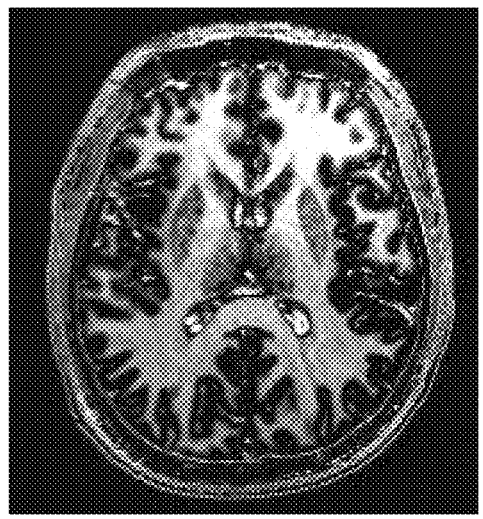
Figure 34A:
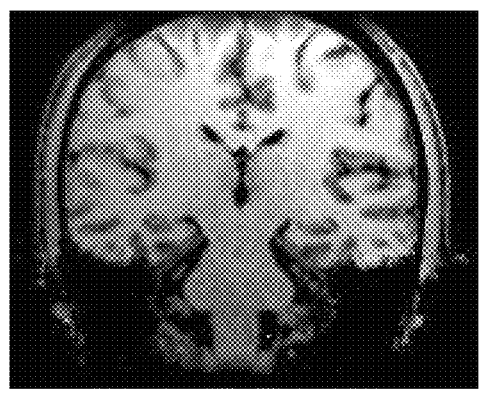
Figure 34B:
Figure 34C:
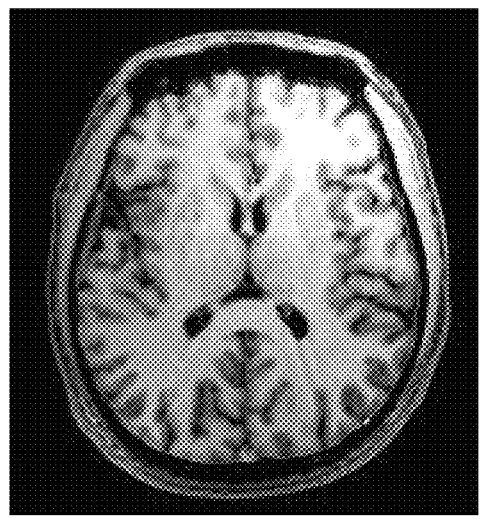
Figure 35A:
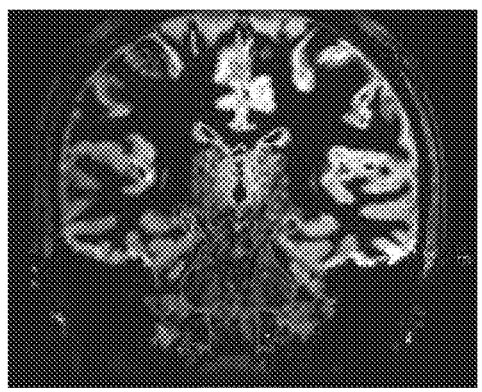
Figure 35B:
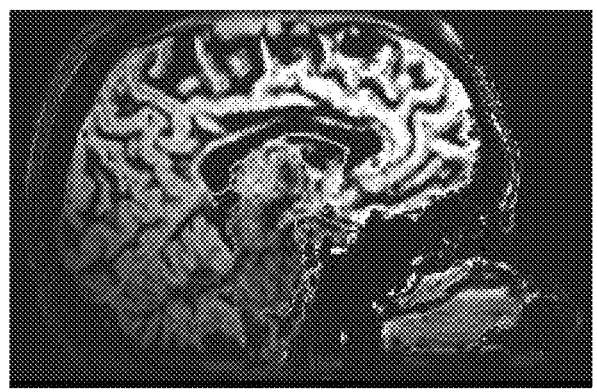
Figure 35C:
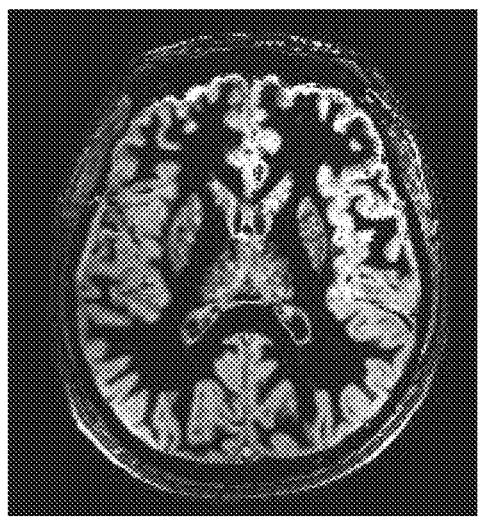
Figure 36A:
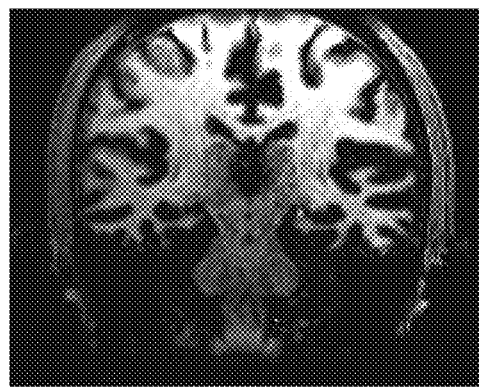
Figure 36B:
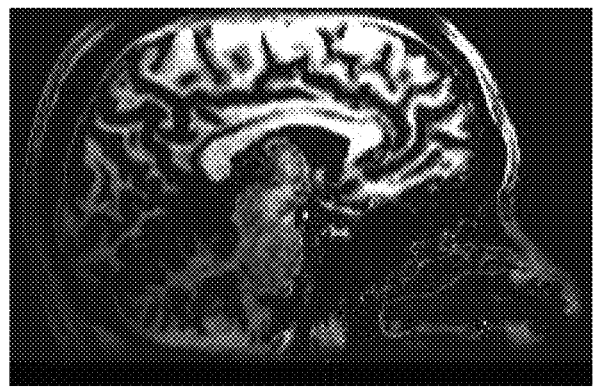
Figure 36C:
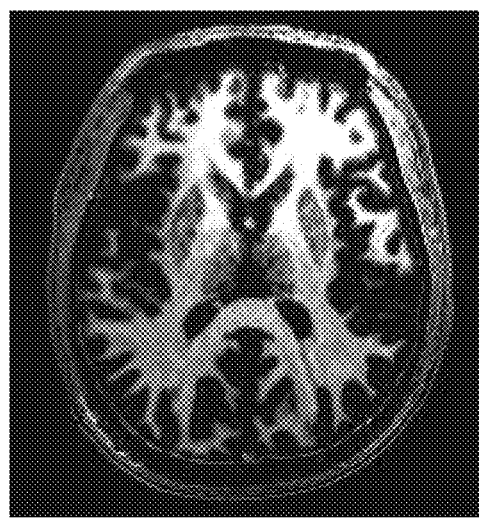
Figure 37A:
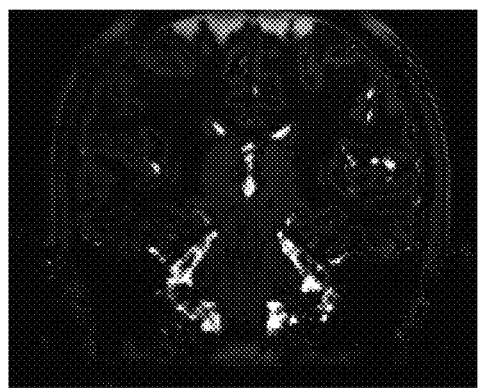
Figure 37B:
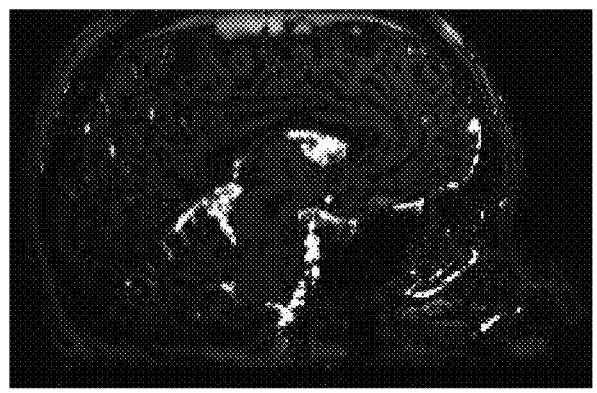
Figure 37C:
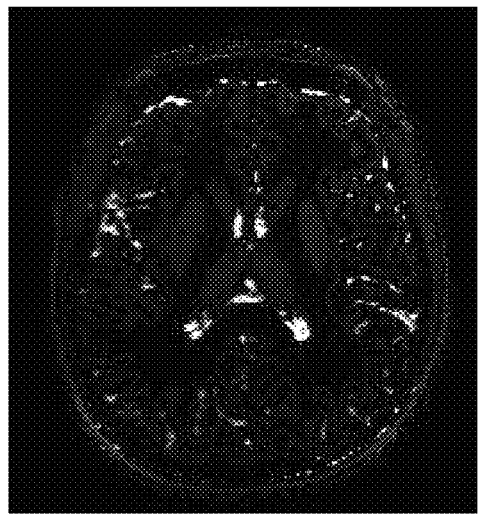
Figure 38A:
Figure 38B:
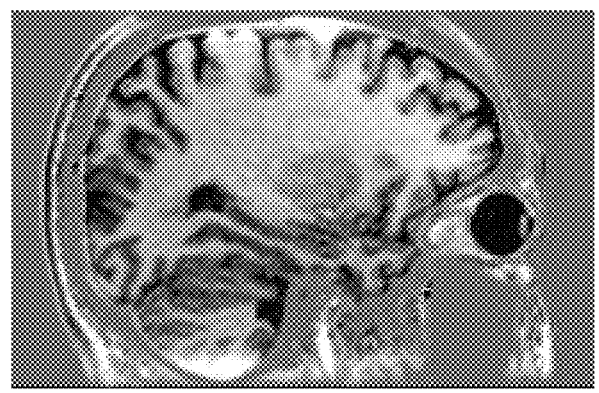
Figure 38C:
Figure 39A:
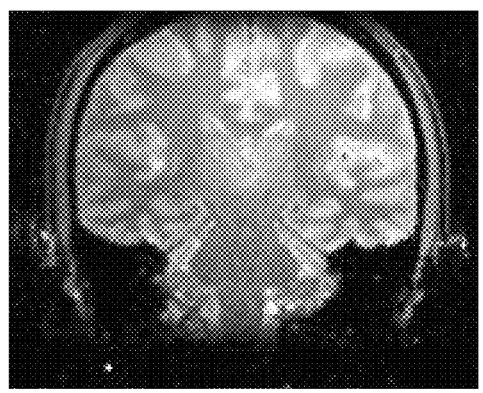
Figure 39B:
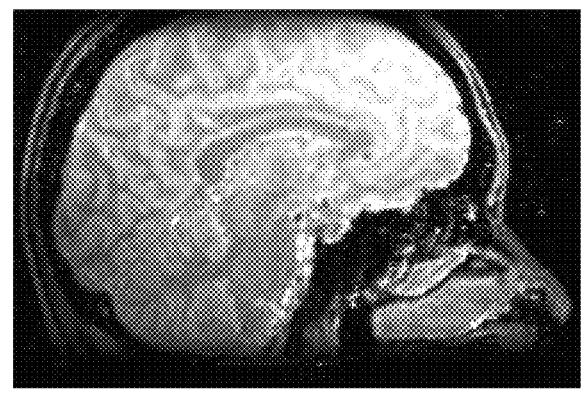
Figure 39C:
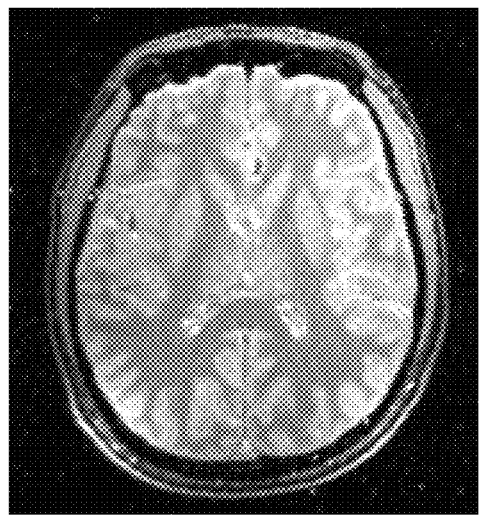
Figure 40A:
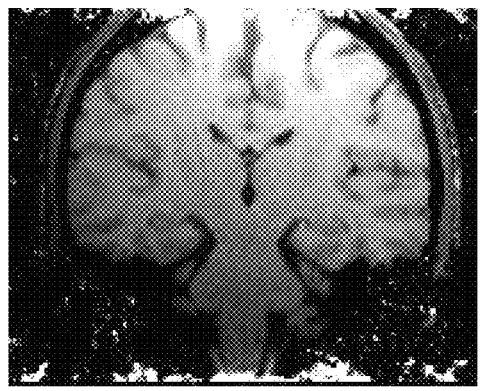
Figure 40B:
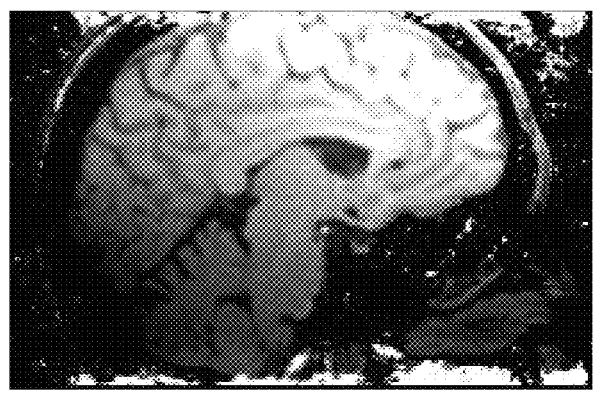
Figure 40C:
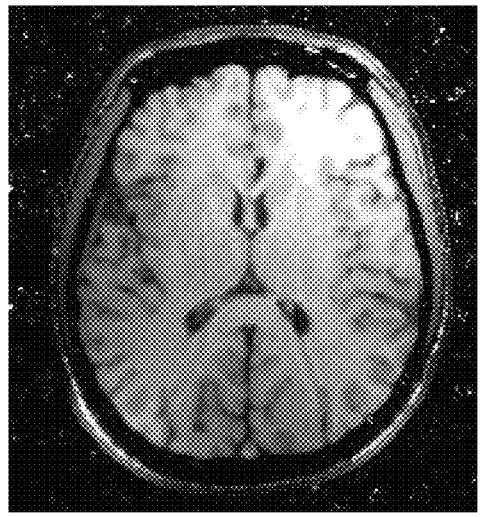
Figure 41A:
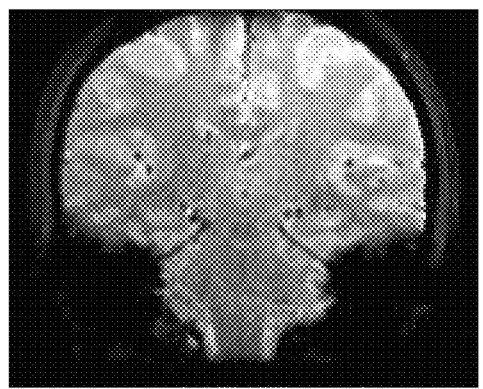
Figure 41B:
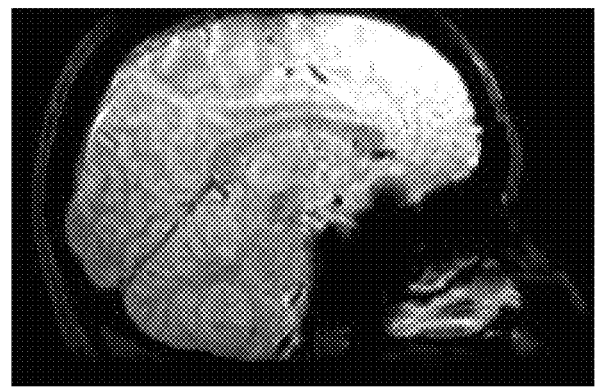
Figure 41C:

FIGS. 31A to 41C illustrate advanced images of the brain. FIGS. 31A to 31C illustrate a virtual saturation recovery T1 weighted image of the coronal plane, the sagittal plane, and the transverse plane of the brain, respectively. FIGS. 32A to 32C illustrate a virtual IR WM nulled image of the coronal plane, the sagittal plane, and the transverse plane of the brain, respectively. FIGS. 33A to 33C illustrate a virtual IR GM nulled image of the coronal plane, the sagittal plane, and the transverse plane of the brain, respectively. FIGS. 34A to 34C illustrate a virtual IR CSF nulled image of the coronal plane, the sagittal plane, and the transverse plane of the brain, respectively. FIGS. 35A to 35C illustrate a virtual double-IR GM image of the coronal plane, the sagittal plane, and the transverse plane of the brain, respectively. FIGS. 36A to 36C illustrate a virtual double-IR WM image of the coronal plane, the sagittal plane, and the transverse plane of the brain, respectively. FIGS. 37A to 37C illustrate a virtual double-IR CSF image of the coronal plane, the sagittal plane, and the transverse plane of the brain, respectively. FIGS. 38A to 38C illustrate a virtual PSIR image of the coronal plane, the sagittal plane, and the transverse plane of the brain, respectively. FIGS. 39A to 39C illustrate a virtual PD weighted image of the coronal plane, the sagittal plane, and the transverse plane of the brain, respectively. FIGS. 40A to 40C illustrate a virtual T1 weighted image of the coronal plane, the sagittal plane, and the transverse plane of the brain, respectively. FIGS. 41A to 41C illustrate a virtual T2* weighted image of the coronal plane, the sagittal plane, and the transverse plane of the brain, respectively.

It should be noted that the above examples illustrated in FIGS. 12A to 41C are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

It will be apparent to those skilled in the art that various changes and modifications can be made in the present disclosure without departing from the spirit and scope of the disclosure. In this manner, the present disclosure may be intended to include such modifications and variations if the modifications and variations of the present disclosure are within the scope of the appended claims and the equivalents thereof.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate a certain variation (e.g., ±1%, ±5%, ±10%, or ±20%) of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable. In some embodiments, a classification condition used in classification is provided for illustration purposes and modified according to different situations. For example, a classification condition that "a probability value is greater than the threshold value" may further include or exclude a condition that "the probability value is equal to the threshold value".

What is claimed is:

1. A system, comprising:
   at least one storage device including a set of instructions for magnetic resonance imaging (MRI); and
   at least one processor configured to communicate with the at least one storage device, wherein when executing the set of instructions, the at least one processor is configured to direct the system to perform operations including:
   acquiring a first set of echo signals and a second set of echo signals relating to a subject, the first set and the second set being generated by applying a first MR pulse sequence on the subject during a scan, the first set being acquired in a first acquisition of the scan, the second set being acquired in a second acquisition of the scan, the first acquisition including at least a first repetition and a second repetition with different repetition times, each of the first repetition and the second repetition having a first flip angle, the second acquisition including at least a third repetition and a fourth repetition with different repetition times, each of the third repetition and the fourth repetition having a second flip angle different from the first flip angle; and
   performing, based on at least one of the first set or the second set, a measurement on the subject, including:
   reconstructing, based on one or more echo signals of the first set or the second set, one or more basic images of the subject;
   generating, based on the one or more basic images, one or more quantitative maps relating to one or more quantitative parameters of the subject; and
   generating, based on the one or more basic images and the one or more quantitative maps, a virtual image of the subject corresponding to a second MR pulse sequence without actually applying the second MR pulse sequence on the subject.

2. The system of claim 1, wherein for each acquisition of the first acquisition and the second acquisition, during each of the repetitions in the acquisition, a plurality of echo signals are acquired at a plurality of echo times.

3. The system of claim 2, wherein:
   the measurement relates to a fat-water separated image of the subject, and
   to perform a measurement on the subject, the at least one processor is further configured to direct the system to perform additional operations including:
   generating, based on at least a portion of echo signals in at least one of the first set or the second set, the fat-water separated image of the subject, the at least a portion of echo signals corresponding to at least one repetition in the first acquisition or the second acquisition.

4. The system of claim 1, wherein:
a flow modulation module is applied on the subject by the MR scanner during at least one repetition in the first acquisition or the second acquisition, the flow modulation module being configured to modulate at least one of a signal intensity or a signal phase of body fluid of the subject.

5. The system of claim 1, wherein:
the measurement relates to a magnetic resonance angiography (MRA) image,
a first flow modulation module is applied on the subject by the MR scanner during at least one repetition in the first acquisition or the second acquisition,
a second flow modulation module different from the first flow modulation module is applied on the subject by the MR scanner during at least one repetition in the first acquisition or the second acquisition, the first flow modulation module and the second flow modulation module being configured to modulate at least one of a signal intensity or a signal phase of body fluid of the subject, and
to perform a measurement on the subject, the at least one processor is further configured to direct the system to perform additional operations including:
generating, based on a first portion of echo signals in at least one of the first set or the second set, at least one first image of the subject, the first portion of echo signals corresponding to the at least one repetition having the first flow modulation module;
generating, based on a second portion of echo signals in at least one of the first set or the second set, at least one second image of the subject, the second portion of echo signals corresponding to the at least one repetition having the second flow modulation module; and
generating, based on the at least one first image and the at least one second image, the MRA image of the subject.

6. The system of claim 1, wherein the measurement relates to a longitudinal relaxation time (T1), and
to perform a measurement on the subject, the at least one processor is further configured to direct the system to perform additional operations including:
determining, based on at least one of the first set or the second set, at least one of an actual flip angle or a B1 transmission field relating to the subject; and
performing, based on the first set, the second set, and the at least one of the actual flip angle or the B1 transmission field relating to the subject, the measurement relating to T1 on the subject.

7. The system of claim 1, wherein the performing a measurement on the subject is based on a multiple dimension integration (MDI) algorithm.

8. The system of claim 1, wherein the measurement relates to a quantitative parameter of a physical point of the subject, and
to perform a measurement on the subject, the at least one processor is further configured to direct the system to perform additional operations including:
determining, based on at least one of the first set or the second set, a signal representation of the physical point, the signal representation being associated with the quantitative parameter; and
determining, based on the signal representation of the physical point, a value of the quantitative parameter of the physical point.

9. The system of claim 8, wherein to determine a signal representation of the physical point, the at least one processor is further configured to direct the system to perform additional operations including:
determining, based on at least one of the first set or the second set, a plurality of signals of the physical point, each of the plurality of signals corresponding to a set of values in a plurality of signal dimensions of signal acquisition using the MR scanner;
determining, among the plurality of signal dimensions, a primary signal dimension and at least one secondary signal dimension, the primary signal dimension being associated with the signal representation; and
determining, based on the plurality of signals, the primary signal dimension, and the at least one secondary signal dimension, the signal representation of the physical point.

10. The system of claim 1, wherein the measurement relates to at least one of a longitudinal relaxation time (T1), a transverse relaxation time (T2), a transverse relaxation decay (T2*), a signal decay rate (R2), a transverse relaxation rate (R2*), a B0 field, a B1 field, an actual flip angle, a proton density (PD), a water fraction, a fat fraction, a virtual image, an MR angiography image, a susceptibility weighted image (SWI), a T1 weighted image, a PD weighted image, an accentuated T1 weighted image, a T2 weighted image, a T2* weighted image, or a quantitative susceptibility map.

11. The system of claim 5, wherein the first flow modulation module is a flow compensation (FC) module, and the second flow modulation module is a dephasing (FD) module.

12. A method implemented on a computing device having at least one processor and at least one storage device for magnetic resonance imaging (MRI), the method comprising:
acquiring a first set of echo signals and a second set of echo signals relating to a subject, the first set and the second set being generated by applying a first MR pulse sequence on the subject during a scan, the first set being acquired in a first acquisition of the scan, the second set being acquired in a second acquisition of the scan, the first acquisition including at least a first repetition and a second repetition with different repetition times, each of the first repetition and the second repetition having a first flip angle, the second acquisition including at least a third repetition and a fourth repetition with different repetition times, each of the third repetition and the fourth repetition having a second flip angle different from the first flip angle; and
performing, based on at least one of the first set or the second set, a measurement on the subject, including:
reconstructing, based on one or more echo signals of the first set or the second set, one or more basic images of the subject;
generating, based on the one or more basic images, one or more quantitative maps relating to one or more quantitative parameters of the subject; and
generating, based on the one or more basic images and the one or more quantitative maps, a virtual image of the subject corresponding to a second MR pulse sequence without actually applying the second MR pulse sequence on the subject.

13. The method of claim 12, wherein for each acquisition of the first acquisition and the second acquisition, during each of the plurality of repetitions in the acquisition, a plurality of echo signals are acquired at a plurality of echo times.

14. The method of claim 13, wherein the measurement relates to a fat-water separated image of the subject, and the performing a measurement on the subject comprises:
    generating, based on at least a portion of echo signals in at least one of the first set or the second set, the fat-water separated image of the subject, the at least a portion of echo signals corresponding to at least one repetition in the first acquisition or the second acquisition.

15. The method of claim 12, wherein:
    a flow modulation module is applied on the subject by the MR scanner during at least one repetition in the first acquisition or the second acquisition, the flow modulation module being configured to modulate at least one of a signal intensity or a signal phase of body fluid of the subject.

16. The method of claim 12, wherein:
    the measurement relates to a magnetic resonance angiography (MRA) image,
    a first flow modulation module is applied on the subject by the MR scanner during at least one repetition in the first acquisition or the second acquisition,
    a second flow modulation module different from the first flow modulation module is applied on the subject by the MR scanner during at least one repetition in the first acquisition or the second acquisition, the first flow modulation module and the second flow modulation module being configured to modulate at least one of a signal intensity or a signal phase of body fluid of the subject, and
    the performing a measurement on the subject comprises:
        generating, based on a first portion of echo signals in at least one of the first set or the second set, at least one first image of the subject, the first portion of echo signals corresponding to the at least one repetition having the first flow modulation module;
        generating, based on a second portion of echo signals in at least one of the first set or the second set, at least one second image of the subject, the second portion of echo signals corresponding to the at least one repetition having the second flow modulation module; and
        generating, based on the at least one first image and the at least one second image, the MRA image of the subject.

17. The method of claim 12, wherein the measurement relates to a longitudinal relaxation time (T1), and the performing a measurement on the subject comprises:
    determining, based on at least one of the first set or the second set, at least one an actual flip angle or a B1 transmission field relating to the subject; and
    performing, based on the first set, the second set, and the at least one of the actual flip angle or the B1 transmission field relating to the subject, the measurement relating to T1 on the subject.

18. The method of claim 12, wherein the performing a measurement on the subject is based on a multiple dimension integration (MDI) algorithm.

19. The method of claim 16, wherein the first flow modulation module is a flow compensation (FC) module, and the second flow modulation module is a dephasing (FD) module.

20. A non-transitory computer-readable storage medium including instructions for magnetic resonance imaging (MRI) that, when accessed by at least one processor of a system, causes the system to perform a method, the method comprising:
    acquiring a first set of echo signals and a second set of echo signals relating to a subject, the first set and the second set being generated by applying a first MR pulse sequence on the subject during a scan, the first set being acquired in a first acquisition of the scan, the second set being acquired in a second acquisition of the scan, the first acquisition including at least a first repetition and a second repetition with different repetition times, each of the first repetition and the second repetition having a first flip angle, the second acquisition including at least a third repetition and a fourth repetition with different repetition times, each of the third repetition and the fourth repetition having a second flip angle different from the first flip angle; and
    performing, based on at least one of the first set or the second set, a measurement on the subject, including:
        reconstructing, based on one or more echo signals of the first set or the second set, one or more basic images of the subject;
        generating, based on the one or more basic images, one or more quantitative maps relating to one or more quantitative parameters of the subject; and
        generating, based on the one or more basic images and the one or more quantitative maps, a virtual image of the subject corresponding to a second MR pulse sequence without actually applying the second MR pulse sequence on the subject.

* * * * *